(12) United States Patent
Belyavsky et al.

(10) Patent No.: US 6,607,914 B1
(45) Date of Patent: Aug. 19, 2003

(54) CAMELLO GENE FAMILY AND USES THEREOF

(75) Inventors: Alexander V. Belyavsky, New York, NY (US); Natalia N. Luchinskaya, Moscow (RU); Anna E. Popsueva, Helsinki (FI)

(73) Assignee: New York Blood Center, Inc., New York, NY (US)

( * ) Notice: Subject to any disclaimer, the term of this patent is extended or adjusted under 35 U.S.C. 154(b) by 0 days.

(21) Appl. No.: 09/593,887

(22) Filed: Jun. 14, 2000

Related U.S. Application Data

(63) Continuation-in-part of application No. 09/333,229, filed on Jun. 14, 1999, now abandoned.

(51) Int. Cl.[7] .......................... C12N 5/00; C12P 21/04; C12P 5/06; A01N 63/00; A61K 38/21
(52) U.S. Cl. .................. 435/325; 435/70.5; 435/320.1; 435/365; 424/85.7; 424/93.21
(58) Field of Search .............................. 435/320.1, 325, 435/365.1, 70.5; 424/93.21, 85.7; 530/351

(56) References Cited

U.S. PATENT DOCUMENTS 5,599,672 A * 2/1997 Liang et al. .................... 435/6

FOREIGN PATENT DOCUMENTS

| JP | 11 332579 | 12/1999 |
|---|---|---|
| WO | WO 00/77024 A1 * | 12/2000 |

OTHER PUBLICATIONS

Gibco BRL Products & Reference Guide, 1997–1998.*
Ozaki; Isolation and mapping of a novel human kidney–and liver–specific gene homologous to the bacterial acetyltransferases, 1998, J. Hum. Genet. 43: 255–258.*
GenBank Accession No. AB013094, 1998.*
Popsueva et al.; Overexpression of Camello, a Member of a Novel Protein Family, Reduces Blastomere Adhesion and Inhibits Gastrulation in Xenopus Laevis, 2001, Development Biology 234: 483–496.*
Ivanova et.al.; Dokl, Akad. Navk, 1998, 359(1): 116–119.*
Ivanova et.al.; Identification of differentially expressed genes by restriction endonuclease–based gene expression fingerprinting, 1995, Nucleic Acids Research, vol. 23: 2954–2958.*
Ozaki K. et al., TSC501 Protein. SWISSPROT Database Accession No. 075839. Nov. 1, 1998.
Nakagawa J. et al., Homo sapiens GLA mRNA, complete cds. EMBL Database Accession No. AB019551. Nov. 16, 1998.
Strausberg R. human EST. EMBL Database Accession No. Al311736. Dec. 14, 1998.
Lee N. H., et al. Rat EST196185. EMBL Database Accession No. AA892382. Apr. 6, 1998.
Marra M.,et al., Mouse EST. EMBL Database Accession No. AA124476. Nov. 23, 1996.
Popsueva AE et al., Homo sapiens putative N–acetyltransferase CML1 mRNA. EMBL Database Accession No. AF187813. Jan. 2, 2000.
Popsueva et al., Homo sapiens putative N–acetyltransferase Camello 2 (CML2) mRNA. EMBL Database Accession No. AF185571. Jan. 2, 2000.
Popsueva AE et al., Rattus norvegicus putative N–acetyltransferase Camello 2 (CML 2) mRNA. EMBL Database Accession No. AF185569. Jan. 2, 2000.
Popsueva AE et al. Rattus norvegicus putative N–acetyltransferase CML3 mRNA. EMBL Database Accession No. AF187814. Jan. 2, 2000.
Popsueva AE et al. Rattus norvegicus putative N–acetyltransferase Camello 4 (cml 4) mRNA. EMBL Database Accession No. AF185570. Jan. 2, 2000.
Popsueva AE et al. Rattus norvegicus putative N–acetyltransferase CML5 mRNA. EMBLDatabase Accession No. AF187100. Jan. 2, 2000.
Popsueva AE et al. Mus musculus putative N–acetyltransferase CML5 mRNA. EMBL Database Accession No. AF187099. Jan. 2, 2000.
Popsueva et al., Camello, a novel gene involved in regulation of Xenopus gastrulation. Developmental Biology, Jun. 1, 1999, vol. 210, No. 1, p. 235, abstract 326.
Ivanova et al., Identification of mRNA, localized at various segments of the Xenopus laevis embryo at early stages of the gastrula. Dokl Akad Nauk., Mar. 1998, vol. 359, No. 1, pp. 116–119.

* cited by examiner

Primary Examiner—Deborah Crouch
Assistant Examiner—Joseph Woitach
(74) Attorney, Agent, or Firm—Amster, Rothstein & Ebenstein

(57) ABSTRACT

The present invention provides a purified and isolated nucleic acid encoding a camello protein. The present invention also provides a vector comprising nucleic acid encoding camello, a host cell transformed with the vector, and a method for producing recombinant camello protein. In addition, the present invention also provides a purified camello protein. Also provided by the present invention is nucleic acid probes and mixtures thereof specific for camello nucleic acid and antibodies immunoreactive with camello. The present invention also provides a methods for screening for agents which bind to the camello protein and the nucleic acid encoding the camello. Finally, the present invention provides a non-human, transgenic model for camello expression.

20 Claims, 21 Drawing Sheets

Xenopus camello (Xcml)

Nucleotide sequence

```
   1 gcacgagcaa gctgctttct cgttatttct tctgttcccc cggaacagga ctcatataag
  61 atccttctgt agttataggt ggaggccttt gctcagtcgg agtatcatgg ccaacgtctc
 121 cataagaaaa tacaaaaaca gtgactatga aacggtcaac ttcttgtttg ttgaaggaac
 181 aaaagagcat ctcccagcag cctgttggaa cacactgaag aagcctcggt tttatttcat
 241 cattattgtg gcatgtgcca gcatcttcat gtgcaccagt tcctatgttc tgtcccttac
 301 aagccttgtt gccctgttgg ctgttggctg gtatggcttg tacttggaat tccatgggta
 361 tgcaagtcgg tgccagcgtg aggatatgct tgatattgag aattcctaca tgatgagtga
 421 caatacttgt ttctgggtgg cagagataga caggaaggtt gtgggcatag tgggtgccaa
 481 accattaaaa gaagcagatg atgagctgtt tctgttacat ctctctgttg ccagggactg
 541 tcgccagcag cggattggca caaagctgtg ccagacagtc attgattttg ccaggcagcg
 601 tggtttcaaa gctgtgtgtc tggaaacagc aaacatacaa gacgcagcaa taaagttgta
 661 tgaagccgtt ggctttaaga aatcccttgt tgcaatcccc ccattccttc ttaaccaata
 721 cacatctttc acagttattt attacagata tgatatcaaa tcataggaaa tccagtgctt
 781 aataatccat aggacacaat cttctgccac cttccatcag caccggccta cagccacatc
 841 aactggtttc atgagcagaa tcagaaccta agatccaaga tgagtctgaa accctacaga
 901 ctggagaaga ggaaccagtt cagatggtta ttactaaatt cattttggaa agccaccatg
 961 gaaggggaag ctccagaagc ctcctgagat gtttcacttt caatgtcaaa agaaaaataa
1021 acagtagaca aactaatatc aacaagtgtg ggatcgactc tgtccacatg atgtggagta
1081 agaaatttaa ccaatcttaa atcaaagctg ggtatcagtc aattttcctt gattttactc
1141 ttagagtttt ttaaacacag gacatgtcat atgcatttct tctgatattc cttcccatgt
1201 cttgctatta aacagcatat ttgtt
```

FIG. 1A

Predicted amino acid sequence

Human camello 1 (Hcml 1)

Nucleotide sequence

```
  1 ccttgggmca gmmttcggca cgagcggcac gagaagcccc agacggtatc tccgagatgc
 61 cagtgagcgg ctgagagctg aagcccctg  gacactcaag gctcttgtgg tgacagtctg
121 acgtaaaggc gtgcagggag gcctagctct gtctcctgga cttagagatt tcagacacag
181 aagtctgtcc atggctcctt gtcacatccg caaataccag gagagcgacc gccagtgggt
241 tgtgggcttg ctctcccggg ggatggccga gcatgcccca gccaccttcc ggcaattgct
301 gaagctgcct cgaaccctca tactcttact tgggggggccc ctcgccctac tcctggtctc
361 tggatcctgg cttctagccc tcgtgttcag catcagcctc ttccctgccc tgtggttcct
421 tgccaaaaaa ccctggacgg agtatgtgga catgacattg tgcacagaca tgtctgacat
481 taccaaatcc tacctgagtg agcgtggctc ctgcttctgg gtggctgagt ctgaagagaa
541 ggtggtgggc atggtaggag ctctgcctgt tgatgatccc accttgaggg agaagcggtt
601 gcagctgttt catctctctg tggacagtga gcaccgtcgt cagggatag caaaagccct
661 ggtcaggact gtcctccagt ttgcccggga ccagggctac agtgaagtta tcctggacac
721 cggcaccatc cagctctctg ctatggccct ctaccagagc atgggcttca agaagacggg
781 ccagtccttc ttctgtgtgt gggccaggct agtggctctt catacagttc atttcatcta
841 ccacctccct tcttctaagg tagggagtct gtgatctctt tctgtgtgta ttggtcagaa
901 tagaatccat tcagctgtag cagcaagcaa tccccaacct ttcactgcaa tgacctttca
961 atgcaataaa agcttattgt ccattcaaaa aaaaaaaaa  aaaaagatc
```

FIG. 2A

Predicted amino acid sequence

Human camello 2 (Hcml 2)

Nucleotide sequence

```
  1 ctggactcag tgacttcaga cacagaagtc tgtccatggc tccttatcac atccgcaaat
 61 accaggagag cgaccgcaag tcggtcgtgg gcttgctctc cggggggatg gccgaacacg
121 cccagccac cttccggcga ttactgaagc tgcctcgaac cctcatactc ttacttgggg
181 gggcccttgc cctactcctg gtctctggct cctggattct ggccctcgtg ttcagcctca
241 gcctccttcc tgccctgtgg ttccttgcca aaaaaccctg gacgcggtat gtagacatag
301 cattgcgcac agacatgtct gacatcacca atcctacct gagtgagtgt ggctcctgct
361 tctgggtggc tgaatctgaa gagaaggtgg tgggcacagt aggagctctg cccgttgatg
421 atcccacctt gagggagaag cggttgcagc tgtttcatct ctctgtggac aatgagcacc
481 gtggtcaggg gatagcaaaa gccctggtca ggactgtcct ccagtttgcc cggaccagg
541 gctacagtga agttgtcctg gacaccagca catccagct ctctgccatg ggcctctacc
601 agagcttggg cttcaagaag acgggccagt ccttcttcca cgtgtgggcc aggctggtgg
661 atcttcatac agttcatttc atctatcacc tcccttctgc tcaggcaggg cgtctatgat
721 ttctttcctt ctgtattggt cagaatagaa tccattcggc tgtagcagca agcaatcccc
781 aacctctgac tgcaatgacc tttctgtgca ataaaagctt attgtccatt
```

FIG. 3A

Predicted amino acid sequence

Human camello 3 (Hcml 3)

Nucleotide sequence (Partial)

```
  1 gcgctgtgct tcgccgtgag ccgctcgctg ctgctgacgt gcctggtgcc ggccgcgctg
 61 ctgggcctgc gctactacta cagccgcaag gtgatccgcg cctacctgga gtgcgcgctg
121 cacacggaca tggcggacat cgagcagtac tacatgaagc cgcccggctc ctgcttctgg
181 gtggccgtgc tggatggcaa cgtggtgggc attgtggctg cacgggccca cgaggaggac
241 aacacggtgg agctgctgcg gatgtctgtg gactcacgtt tccgaggcaa gggcatcgcc
301 aaggcgctgg gccggaaggt gctggagttc gccgtggtgc acaactactc cgcggtggtg
361 ctgggcacga cggccgtcaa ggtggccgcc cacaagctct acgagtcgct gggcttcaga
421 cacatgggcg cc
```

FIG. 4A

Predicted amino acid sequence

Mouse camello 1 (Mcml 1)

Nucleotide sequence

```
   1 attcggcacg acggctaaaa tggaagtgga gcggactcct agtaccgcta gaagctgctg
  61 gcggaggaca aggagaacta actctaattt gtcccggctt cggaggtgga aaagccccca
 121 ctggtcgggc ctagaagctg agggttcaag gaaggtgtgc aaggcaggta tagctgtctc
 181 tcctggatgc caagatttga gacccagaag tctcccatgg ttccttatca catccgacag
 241 taccaggaca gcgaccataa aagagtcgtg gatgtgttca ccaagggcat ggaggagtac
 301 attccctcta cctttcggca catgcttatg ctgccccgaa ccctcctgct cttacttggg
 361 gtgccccttg ccctggtcct ggtgtctggc tcctggatcc tggctgttat ttgcatcttc
 421 tttctgctcc tacttctgcg gctccttgcc agacagccct ggaaggaata tgtggccaaa
 481 tgtttgcaga cagacatggt tgacatcacc aagtcttacc tgaatgtaca tggcgcctgc
 541 ttctgggtgg ctgagtctgg ggggcaggtg gtgggcatag tggctgctca gccagtcaag
 601 gatcctccac tagggaggaa gcagctgcag ctctttcgcc tgtctgtgtc ctcacagcat
 661 cgaggacagg ggatagcgaa agcgctgacc agaactgtcc tccagtttgc aagggaccag
 721 agttacagtg atgttgtcct tgagaccagc gccttgcagc aaggtgctgt gactctctac
 781 ctgggcatgg gcttcaagaa ggcaggccag tacttcatga gtatattctg gaggttagca
 841 ggtatttgta caattcaatt aaagtactcc ttcccttctg cctaggaggg gtggctgtga
 901 ccttatgctc ctgtgcagca agcacacttc tctgcactct gctacaggaa ccagtgaacc
 961 ctgtcatgtc agtgtgatta acaataaaag ttgttggtgc acaccaaaaa aaaaaaaaaa
1021 aaaaaaa
```

FIG. 5A

Predicted amino acid sequence

Mouse camello 2 (Mcml 2)

Nucleotide sequence

```
   1 gaggttcacc aggctctggt aggttttact ggatgtcatc ggaggcaaag gccatcctgg
  61 acatttggat ctgtcatatt agactgaatc attccagttg ctggaaagag gatttgttga
 121 aacttggacc tgggaacaca ggagttttca actctgggcc ctgaagagga aacagaagat
 181 ctcagaacag cacatctttc cacagtgtag aacctcagtt cccaaagggc tcagggaagt
 241 tatgcaagaa ggtctggatg tcccttgtga tcactgatac ttgagagcca gaagtctccc
 301 catggctgct tatcacatcc gacagtacca ggagaaggac cacaaaaggg tcctggaatt
 361 gttctccagc ggcatgaagg agcttattcc tgctgccatc cgacagatgc tgacactgcc
 421 tcattctctc ttgctcttac ctggagtgcc tgtgaccata gtattgatgt ctgcctcctg
 481 gctcctggcc acattataca gcttcctctt tctcctttgc ctgtggctta ttttctggat
 541 ttcttgcaga aattatgtgg ctaaaagttt gcaggcagat cttgctgaca tcaccaagtc
 601 ttacctgaat gcacatggct ccttctgggt ggctgagtct ggagaccaag tagttggcat
 661 ggtgggtgct cagccagtca aggaccctcc attagggaag aagcagatgc agctctttcg
 721 cctgtctgtg tcctcacagc atcgaggaca gggaatagca aaggcactgg tcagaactct
 781 cctccagttt gctcgggacc agggttacag tgatgttgtc cttgagactg gcagtgtgca
 841 acatagtgct caggctctct accaggccat gggcttccag aagacaggcc agtactttgt
 901 cagtataagc aagaagttaa tgggtctttc tattcttcaa ttctcttact ctctcccttt
 961 tgcttcagga ccagggtata gtgggaaata tttaaaaaaa ggtcccattc catgctagca
1021 ccaggtactc tctggcccca gtggtctcac tgcctccatg gcttgtccta tgtagcaact
```

FIG. 6A

Predicted amino acid sequence

Mouse camello 3 (Mcml 3)

Nucleotide sequence

```
  1 attcggatcc atggcacagc attaaggctg atttggaccc tgagctctga gcaactagtc
 61 taaatgttca gagctgatgg gaaatggctt tgttgaaact tgatcttgga aatcctgcat
121 ttgcaatgta tatactctag agaaagagat caaaggagct gggcatgaag actggtggcc
181 tcaagggtta cagggaaacc tacagtcaga agcagctgtg tctttggtct ttgagatctt
241 agcctccgaa gtctcccatg gctccttatc atatccgaaa ataccaggac agcgaccaca
301 ggagtgtggt ggatttgttc cgcagaggca tggaggagca catccccgct acctttcgcc
361 acatgctgct gctgccccga accctcctgc tcttactcgg ggtccctctt actctattcc
421 tggcctcagg ttcctggctt ctggttcttc tgtccatcct taccctcttt ctttccctgt
481 ggttccttgc aaaatacaca tgggaaaagc atgtgatgaa ctgtttgcac acagacatgg
541 ctgacatcac cagaacctac ctgagttctc actcctcctg cttctgggta gctgagtcta
601 gaggtcagac agtgggcatg gtggctgctc ggccagtgaa ggaccccctc ctgcagaaga
661 agcaactgca gctacttcac ctctctgtgt cattgcagca ccgaagagaa ggcctaggga
721 aagctatggt caggactgtc ctccaatttg cacagatgca gggcttcagt gaagttgtcc
781 tttccaccag catgctgcag tacgcagccc tggctctcta ccagggcatg ggcttccaga
841 agactggcga gaccttctac acctatttgt ccagactaag gaaatctcca atgataaact
901 taaagtatag cctcacttct cgggaagggg acctgtga
```

FIG. 7A

Predicted amino acid sequence

Mouse camello 4 (Mcml 4)

Nucleotide sequence

```
  1 ttcggatcca tgggacactc ggctgtagta gcagctaaga ggacagagag acaagggctg
 61 cgaggcacaa atataaacag atctggtgtc tctcatggat gctgagattt gagacgaagt
121 ttccccatgg cttcttttcg catccgccag ttccaggaga gggactacaa acaggtcgtg
181 gatgtgttct ccaggggcat ggaggagcac atacccactg ccttccgcca cttgctgaca
241 ctgccccgaa ccctcctgct cttagctgtg gtgccccttg ccatagtcct ggtgtctggc
301 tcctggttcc tggctgttgt atgcattttc tttctgttcc tattcttgtg gttcctcgcc
361 agcaagccct ggaagaatta tgtgtccaaa tgtttacaca cagacatggc tgacatcacc
421 aagtcctacc tgagtgtccg tggctcaggt ttctgggtgg ctgagtctgg ggggcaggtg
481 gtgggtacag tggctgctcg gccagtcaag gatcctccgt tagggaggaa gcagctgcag
541 ctctttcgcc tgtctgtgtc ctcacagcat cgaggacagg ggatagcgaa agcgctgacc
601 agaactgtcc tccagtttgc aagggaccag ggttacagtg atgttgtcct tgtgactggc
661 cttttgcagc aaggtgctgt gactctctac tacagcatgg gcttccagaa gacaggtgaa
721 tccttcgtgg acatactcac atggcttgtg gatgtttctc taattcattt catataccca
781 ctcccttctg ctcaaaaata tgagttgtga tctctctcag tgtgtctgtc agcctctggt
841 ttactatgct gtgggaataa ataccccaga gattgtggtg gacaaatcaa aaaaaaaagg
901 aaa
```

FIG. 8A

Predicted amino acid sequence

Mouse camello 5 (Mcml 5)

Nucleotide sequence (Partial)

```
  1 caaagtgcta taoccctcta tgaggctatg ggattccaaa ggacaggaaa atactcagag
 61 atcagcatta tcaaatggtt aattacattt tctataattc atttcacata ttctttccct
121 tctactcaga aacatgaact ataatcttat ttcttaccat atagatcagg ttccaattac
181 tgtactgtaa taataataa aagcatattt ttcatgctca ccggattact acttgacaat
241 gttagggtga caaagttgac ctctacagtg cacagccctt ctccatgaga catttgtttc
301 atctttgaga tcctttccgg gggctacttt gcatctctac tcttattaaa ctgagcat
```

FIG. 9A

Predicted amino acid sequence

Rat camello 1 (Rcml 1)

Nucleotide sequence

```
  1 ttcggcacga ggccactgaa tgccactaga agctgatgcc attccagaca ctctaggttg
 61 tgtagtagcg ggactcaggg aaggagtgtg ggcaagtgaa tgctgagatt tgagacccag
121 aagtttctcc catggtttct tatcacatct gcgagtacca agacagcgac tataaaagtg
181 ttgtggatgt gtttaccaag ggtgcagaag agtacatccc ctccaccttc cgccacttgc
241 tgctgctgcc ccgaaccctc ctactcttac ttggggtgtc ccttgccctg gtcctggtgt
301 ctggctcctg gctgctggct gttgtatgca tcttttttct gctcccattt ttgtggttcc
361 ttgctggaca gccctggaag aattatgtgt ccaaatgttt acacacagat atggctgaca
421 tcaccaagtc ttatctgagt gatcgtggct caggtttctg ggtggctgag tctggggagc
481 aggtagtggg cacagtgggt gctctgccag tcaaggagcc tccatcaggg aggaagcagt
541 tgcagctctt ccacctggct gtgtcctcac agcatcgagg acagggata gcgaaagcac
601 tggtcagaac tgtgctccag tttgcacggg accagggcta cactgatgtt gtccttgaga
661 ctagcaccat gcagataggt gctgtgaccc tctacctggg catgggtttc cagaagacag
721 gccaatactt cccgagtatg ctctggaggt tagtgggtat tcgttttgtt caactaaatt
781 actccttccc ttctgcctag gaagggaggc tgtgaccttg agttcctgtg gagcaagcac
841 acttccctgc actctgctac aggaaccagt gaaccctgtc atgtcagtgt gattaacaac
901 aaaagcttgt tgctgc
```

FIG. 10A

Predicted amino acid sequence

Rat camello 2 (Rcml 2)

Nucleotide sequence

```
  1 tcccggcttc ggaagcagaa agcaccctac aggttgggcc tagtagttga gggttcaggg
 61 ataggtatag ctgtctctcc tggatgccaa gatttgagac ccagaagtct cccatggctc
121 cttatcacat ccgccagtac caagacagcg accacaaaag tgtcgtggat gtgttcacca
181 agggcatgga agaacacatc ccctccacct tccgccacat gcttatgctg ccccgaaccc
241 tcctactctt acttggggtg ccccttgccc tggtcctggt gtctggctcc tggctgctgg
301 ctgttgtatg catcttcttt ctgctcctac tcctgcggtt ccttgctgga cagccctgga
361 aggagtatgt ggctacatgt tgcggacag acatggctga catcaccaag tcttacctga
421 atgcacatgg ctccttctgg gtggctgagt ctggaaacca ggtggtgggc atagtggctg
481 ctctgccagt caaggatcct ccatcaggga ggaagcagct gcagctcttt cgcctgtctg
541 tgtcctcaca gcatcgagga caggggatag cgaaagcact ggtcagaact gtcctccagt
601 ttgcacggga ccagggctac actgatgttg tccttgagac cagtaccttg caacaaggtg
661 ctatgaccct ctacctgggc atgggcttcc agaagacagg ccaacgcttc ctgactatgt
721 tctggaggtt agtgggtatt cggacaattc aattaaagta tcccttccct tctgcctagg
781 aaaggggct gtgaccttga gttcctgtgg agcaagcatg cttctctaaa ctctgctaca
841 ggaaccagtg aaccctgtca tgtcagtgtg attaacaata aaagcttgtt gctgcacacc
```

FIG. 11A

Predicted amino acid sequence

Rat camello 3 (Rcml 3)

Nucleotide sequence (Partial)

```
  1 tgtcaggcca agaattcggc acgaggagga cagcgaccac aggagtgtag tgaatttgtt
 61 ctgcagaggc acggaggagc acatctccgc cagcttccgc tacatgctgc tgctgcccgg
121 aaccctcctg atcttactcg gggtccctct tactctattc ttggcctcag gctcctggct
181 tctggttctt ctgtccaccc taaccctcct tgtttccctg tggctccttg caaatacccc
241 ttgggagaag tatacggcaa tgtgtttgca ctcagacatg gctgatatcc cagaaccta
301 cttgagttct cattactcct gcttctgggt ggctgagtct agaggtcaga tggtgggcat
361 aatcgctgtt ttaccagtga aggatcccct cctgcagagg aagcaactgc agctacgtca
421 cctctctgtg tccctggagc accggagaga ggggattgga agagctatgg tcaggactgc
481 cctccagttt gcagagatgc agggcttcag tgaagttgtc ctggtcacca gcatgttgca
541 gtatgctgcc ctagctctgt accagagcat gggcttccag aagactggtg agttcttcta
601 tacctttgtc tctcgactaa ggaattctcc aatgatatgc ttaaaatatt gcctcacttc
661 tgctctgaat gacctgaaaa cctgaaagac ctgctctgag agacctgtga gctctctcct
721 gtggccatca gtcaggatct aattgcttct gtaatagtaa caagcaaacc cagctatttc
781 agcaaaccac tgaccctcac tctcaagcac atcggaataa atgtttgtgg atggggttgg
841 ggcaatggct actctttgtt atccatgctt ttctgaggta tcctttagct aatactacaa
901 tcatatataa aaagtaacgc agataataaa atttaactta gcttgtg
```

FIG. 12A

Predicted amino acid sequence

Rat camello 4 (Rcml) 4)

Nucleotide sequence

```
  1 agacgaaggt ttcccatggc ttcttttcac atccgccagt tccaggagag ggactatgaa
 61 caggtcgtgg atatgttctc caggggaatg aaggaacaca tccccactgc cttccgccac
121 ttgctgctgc tgccccgaac cctcctactc ttacttgggg tgccccttgc cctggtcctg
181 gtgtctggct cctggctgct ggctgttgta tgcatcttct ttctgctccc attttttgtgg
241 ttccttgctg gacagccctg gaagaattat gtgtccaaat gcttacacac agacatggct
301 gacatcacca agtcttatct gagtgatcgt ggctcaggtt tctgggtggc tgagtctggg
361 ggccagatag tgggcacagt gggtgctctg ccagtcaagg atcctccatc agggaggaag
421 cagttgcagc tcttccgcct gtctgtgtcc tcacagcatc gaggacaggg gatagcgaaa
481 gcactggtca gaactgtgct ccagtttgca cgggaccagg gctacacgga tgttgtcctt
541 gtgactggcc ttttgcagca aggtgctgtg accctctact acagcatggg cttccagaag
601 acaggcgaat ccttcatgga catactcaca tggcttgtgg atgtttctct aattcatttc
661 atatacccgc tcccttcctc ctgagaacct gagtttcgat ccctctgtgt gtctgtcagc
721 ctctggttca ctgtgctgtg ggaacaaata atcctgatat tgtagtggac aaatcaccc
```

FIG. 13A

Predicted amino acid sequence

Alignment of amino acid sequences of camello protein family members

```
              1                                                                        80
Hcml    1 (1) MAPCHIRKYQESDRQMWGLLSRGVAEHAPATFRQLLKLPRTLILLLGGPLALLLVSGSWLLALVFSISLFPALWFLAKK
Hcml    2 (1) --------------------------------------------------------------------------------
Hcml    3 (1) MVPYHIRQYQDSDHKRVVDFTKGMEEYIPSTFRHMLMLPRTLLLLLLLLGVPLALVLVSGSWTLAVICIFFLLLLRLLARQ
Mcml    1 (1) MAAYHIRQYQEKDHKRVLELFSSGWKELIPAAIRQMLTLPHSLILLLLPGVPVTIVLMSASMLLATLYSFLFLCCLWLIFWI
Mcml    2 (1) MAPYHIRKYQDSDHRSVVDLFRRGMEEHIPATFRHMLLLPRTLLFLLLLGVPLTLFLASGSWLVLLSILTLFLSLWFLAKY
Mcml    3 (1) MASFRIRQFQERDYKGQWDVFSRGMEEHIPTAFRHLLTLPRTLLLLLLAVVPLAIVLVSGSWFLAVVCIFFLFLWFLASK
Mcml    4 (1) --------------------------------------------------------------------------------
Mcml    5 (1) MVSYHICEYQDSDYKSVVDFTKGAEEYIPSTFRHLLLLLLPRTLLLLLLGVSLALVLVSGSWLLAVVCIFFLLPFLWFLAGQ
Rcml    1 (1) MVRPRIRHEEDSDHRSWNLFCRGTEEHISASFRYMLLPGTLLILLGVPLTLFLASGSMLLVLLSTLTLLVSLWLLAKY
Rcml    2 (1) --------------------------------------------------------------------------------
Rcml    3 (1) --------------------------------------------------------------------------------
Rcml    4 (1) MANVSIRKYKNSDYETVNFLFVEGTKEHLPAACWNTLKKPRFYFIIVACASIFMCTSSYVLSLTSLVALLAVGWYGLYL
Xcml    1 (1) --------------------------------------------------------------------------------
Consensus (1) M   IR Y D DH   W LF  G  EHIPA  R ML LP TLLLL    L L L SGSWLL    L     LW LA
                                                         Hydrophobic domain 81                                                                       160
Hcml    1 (81) PWTEYVDMTLCTDMSDITKSYLSERGSCFWVAESEEKVVGMVGALPVDDPTLREKRLQLFHLSVDSEHRRQGIAKALVRT
Hcml    2 (1)  --------------------------------------------------------------------------------
Hcml    3 (31) VIRAYLECALHTDMADIEQYYMKPPGSCFWVNHGACFWVAESGGQWGIVAARAHEE----DNTVELLRMSVDSRFRGKGIAKALGRK
Mcml    1 (81) PWKEYVAKCLQTDMVDITKSYLNVHGACFWVAESGGQWGIVAAQPVKDPPLGRKQLQLFRLSVSSQHRGQGIAKALTRT
Mcml    2 (81) SCRNYVAKSLQADLADITKSYLNAHGS-FWVAESGDQWGMVGAQPVKDPPLGKKQWQLFRLSVSSQHRGQGIAKALVRT
Mcml    3 (81) TWEKHVMNCLHTDMADIIRTYLSSHSSCFWVAESRGQTVGMWAARPVKDPPLLQKKQLQLLHLSVSLQHRREGLGKAMVRT
Mcml    4 (1)  --------------------------------------------------------------------------------
Mcml    5 (81) PWKNYVSKCLHTDMADITKSYLSDRGSGFWVAESGGQWGTVGALPVKEPPSGRKQLQLFHLAVSSQHRGQGIAKALVRT
Rcml    1 (81) --NQVVGIVAALPVKDPPSGRKQLQLFRLSVSSQHRGQGIAKALVRT
Rcml    2 (1)  --------------------------------------------------------------------------------
Rcml    3 (81) PWEKYTAMCLHSDMADIPRTYLSSHYSCFWVAESRGQWWGIIAVLPVKDPLLQRKQLQLRHLSVSLEHRREGIAKALVRT
Rcml    4 (81) EFHGYASRCQREDMLDIENSYMWSDNTCFWVAEIDRKVVGAKPLKEA---DDELFLLHLSVARDCRQQRIGTKLCQT
Xcml    1 (81) W  YV  L  TDMADI KSYL      S  FWVAES  QWVGIVAA  PVKDP  RKQLQLF  LSVSS HRGQGIAKALVRT
                  Motif D                                                Motif A
```

```
                    161                                                                                           240
Hom1    1  (161)    VLQFARDQGYSEVILDTGTIQLSAMALYQSMGFKKTGQS-FFCVWARLVALHTVHFIYHLPSSKVGSL-------------------
Hom1    2   (26)    VLQFARDQGYSEWLDTSNIQLSAMGLYQSLGFKKTGQS-FFHVWARLVDLHTVHFIYHLPSAQAGRL-------------------
Hom1    3  (107)    VLEFAVHNYSAVVLGTTAVKVAAHKLYESLGFRHMGA----------------------------------------------
Mom1    1  (161)    VLQFARDQSYSDVVLETSALQQGAVTLYLGMFKKTGQY-FMSIFWRLAGICTIQLKYSFPSA---------------------
Mom1    2  (160)    LLQFARDQGSYDVVLETGSVQHSAQALYQAMGFQKTGQY-FVSISKKLMGLSILQFSYSLPFASGPGYSGKYLKKGPIPC
Mom1    3  (161)    VLQFAQMQGFSEWVLSTSMLQYAHGALYQQGFGFQKTGES-FYTYLSRLRKSPMINLKYSLTSREGDL---------------
Mom1    4  (161)    VLQFARDQGYSDWLVTGLLQQGAVTLYSMGFQKTGES-FVDILTWLVDVSLIHFIYPLPSAQKYEL-----------------
Mom1    5    (1)    --------QSAITLYEAMGFQRTGKYSEISIIKWLITFSIIHFTYSFPSTQKHEL-----------------------------
Rom1    1  (161)    VLQFARDQGYTDWLETSTMQIGAVTLYLGMGFQKTGQY-FPSMLWRLVGIRFVQLNYSFPSA---------------------
Rom1    2   (46)    VLQFARDQGYTDWLETSILQQGAMTLYLGMGFQKTGQR-FLTMFWRLVGIRTIQLKYPFPSA---------------------
Rom1    3  (161)    ALQFAEMQGFSEWLVTSMLQYAALALYQSMGFQKTGEF-FYTFVSRLRNSPMICLKYCLTSA-LNDLKT-------------
Rom1    4    (1)    -----GYTDWLVTGLLQQGAVTLYYSMGFQKPGES-FMDILTWLVDVSLIHFIYYRYDIKS---------------------
Xcm1       (158)    VIDFARQRGFKAVCLETANIQDAAIKLYEAVGFKKSLVAIPPFLLNQYTSFTVIYYRYDIKS---------------------
Consensus           VLQFARDQGYSDWLETS LQ GAV LY SMGFQKTG    F SIL RLV I II F Y LPSA
                                                          Motif B
```

FIG. 14-2

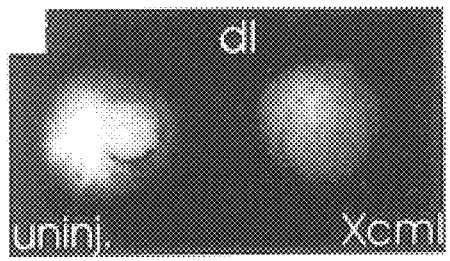
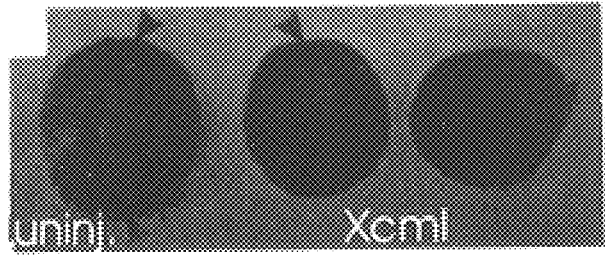
FIG. 16A  FIG. 16B
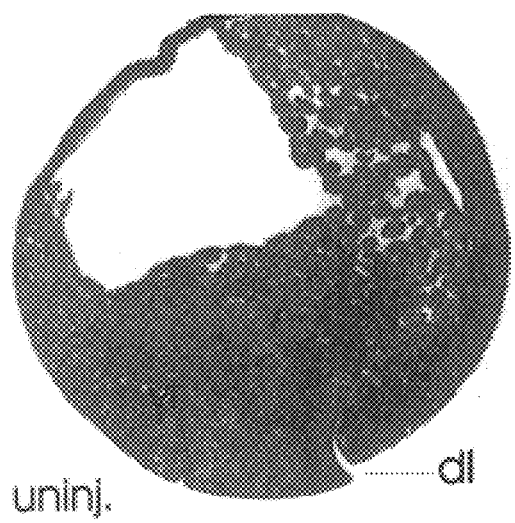
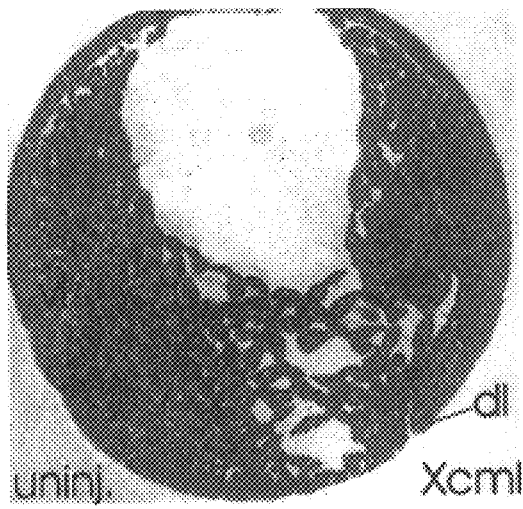
FIG. 16C  FIG. 16D

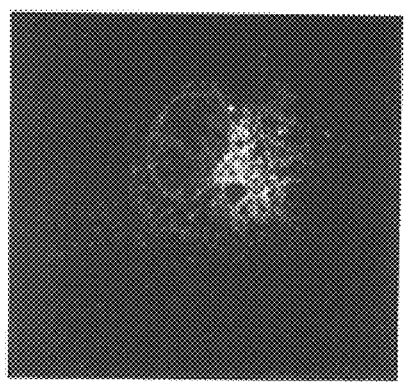
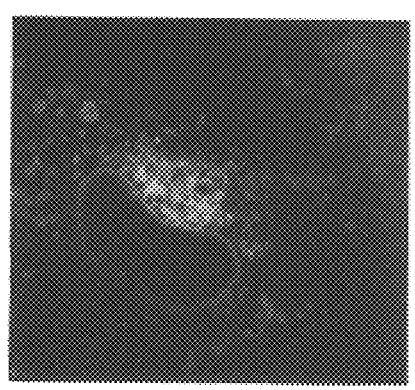
FIG. 18A     FIG. 18B
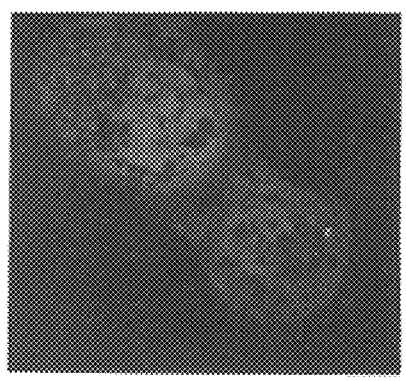
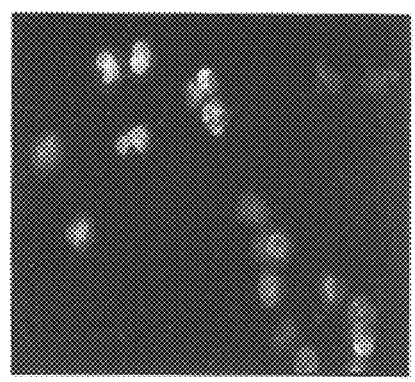
FIG. 18C     FIG. 18D
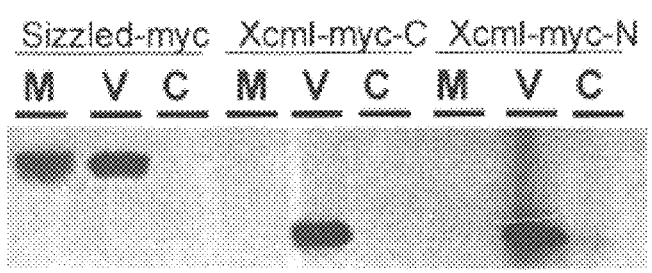
FIG. 18E

CAMELLO GENE FAMILY AND USES THEREOF

CROSS-REFERENCE TO RELATED APPLICATIONS

This is a continuation-in-part of U.S. application Ser. No. 09/333,229, filed Jun. 14, 1999, now abandoned the contents of which are hereby incorporated by reference in their entirety.

BACKGROUND OF THE INVENTION

Vertebrate gastrulation involves complex coordinated regulated movements of cells and cell layers to establish the axial structures and the general body plan. Adhesion molecules and the components of extracellular matrix participate in this process. However, other components and detailed mechanisms of the control of gastrulation movements remain largely unknown. For instance, perturbation of cell adhesion by interference with function of different cadherins or extracellular matrix proteins (Kim, et al., *Development* 125, 4681–4691 (1998); Kuhl, et al., *Mechanisms of Development* 54, 71–82 (1996)) has been shown to lead to certain defects in gastrulation. As such, the elucidation of a protein and its nucleic acid involved in cell adhesion may be useful as diagnostic indicators for certain birth defects.

Adhesion molecules mediate cell to cell and cell to matrix interactions and are essential for numerous physiological and pathological processes. The first step of metastasis is the detachment of the tumor cells from the primary tumor and subsequent access to the circulation such as lymph or blood. Although the exact mechanism is unclear at this time, it has been demonstrated that the loss of certain adhesion molecules, such as certain of the cadherins, is associated with the penetration of tumor cells into other tissues and the increased incidence of metastasis, perhaps by facilitating the detachment of the tumor cells from the primary tumor. Accordingly, the elucidation of a protein and its nucleic acid involved in cell adhesion may be useful as a target for anti-metastatic agents.

SUMMARY OF THE INVENTION

The present invention is based upon the discovery of a novel gene family, hereinafter denoted "the camello gene family" that the inventors believe is involved in embryogenesis and cell adhesion. This discovery may provide useful targets for anti-metastatic agents, as well as diagnostic indicators for birth defects.

Accordingly, the present invention provides a purified and isolated nucleic acid encoding a camello protein. The present invention also provides a vector comprising this nucleic acid and a host cell transformed by this vector. Also provided by the present invention is a nucleic acid probe which hybridizes to nucleic acid encoding camello, a mixture of nucleic acid probes each of which hybridizes to nucleic acid encoding camello and a kit comprising one or more nucleic acid probes which hybridize to nucleic acid encoding camello.

The present invention also provides a method for producing recombinant camello comprising growing a host cell transformed with a vector comprising nucleic acid encoding camello in culture and recovering the recombinant camello from the culture. The present invention further provides a purified camello protein or an analogue thereof, as well as an agent that binds to the camello protein or its analogue, including but not limited to an antibody immunoreactive with camello or an analogue thereof. In addition, the present invention provides a kit comprising an agent that binds to the camello protein.

The present invention also provides a method for screening an agent that binds to the nucleic acid encoding a camello protein comprising contacting the nucleic acid with an agent of interest and assessing the ability of the agent to bind to the nucleic acid. The present invention further provides for a method for screening an agent that inhibits the expression of the nucleic acid encoding a camello protein comprising contacting a cell transformed with a vector comprising the nucleic acid, and assessing the effect of the agent on expression of the nucleic acid. The present invention still further provides a method for screening for an agent that binds to a camello protein or an analogue thereof comprising contacting the protein with an agent of interest and assessing the ability of the agent to bind to the protein.

In addition, the present invention provides a method for determining the aggressiveness of a tumor in a subject comprising detecting abnormal levels of a camello protein in the tumor relative to normal physiological levels of camello in normal tissue. Further, the present invention provides a method for the diagnosis of birth defects comprising detecting abnormal levels of a camello protein in embryological tissue relative to normal physiological levels of camello.

The present invention also provides a recombinant viral vector capable of introducing nucleic acid encoding camello into a target cell such that the target cell expresses camello, the vector comprising (a) nucleic acid of or corresponding to at least a portion of the genome of a virus, the portion being capable of infecting the target cell, and (b) nucleic acid encoding a camello protein operably linked to the viral nucleic acid. Finally, the present invention provides a non-human, transgenic animal model comprising mutated nucleic acid encoding camello incorporated into at least some of the somatic cells of the animal. Additional objects of the present invention will be apparent from the description which follows.

BRIEF DESCRIPTION OF THE FIGURES

Figures 1A, 1B:
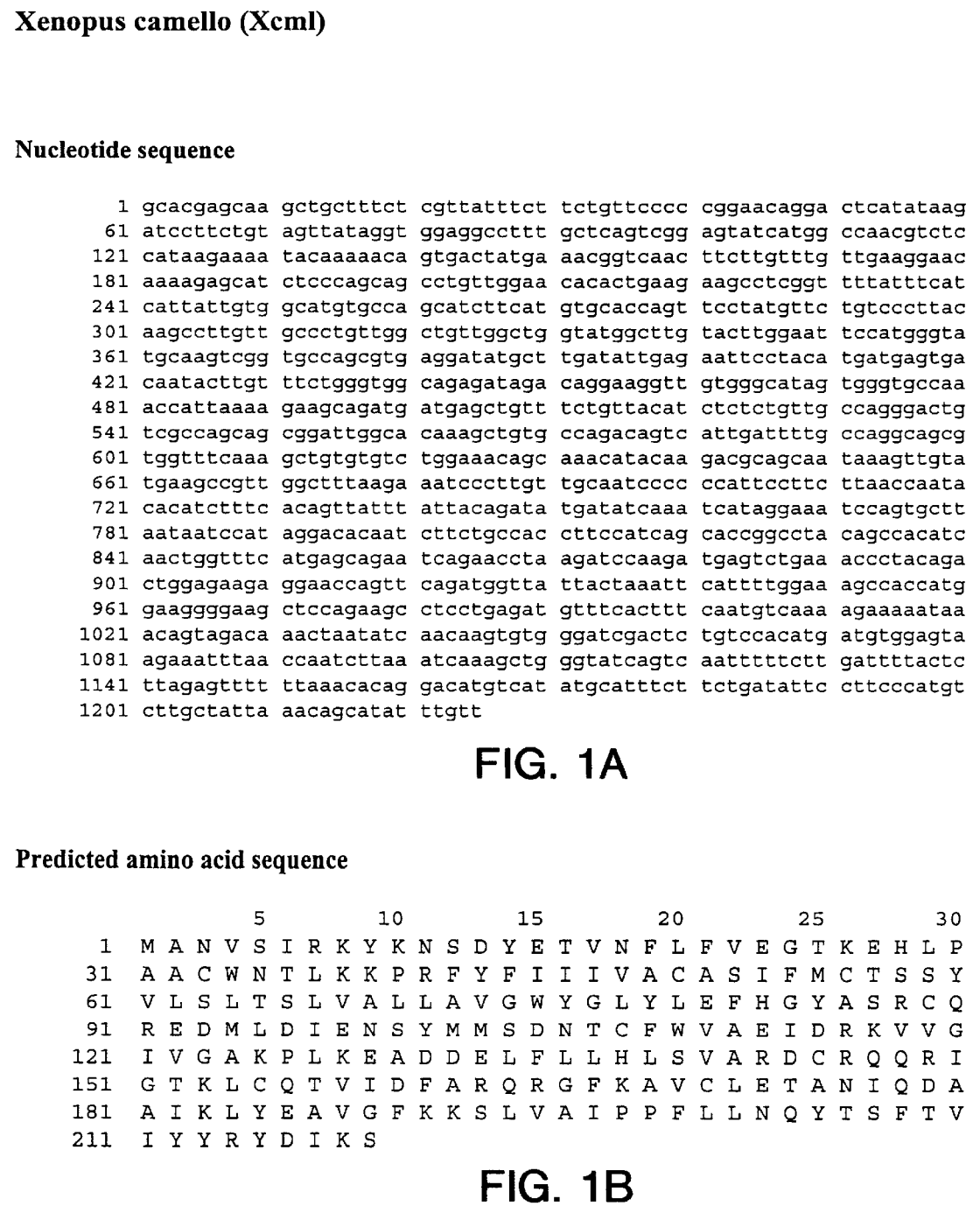

FIG. 1A depicts the nucleotide sequence of Xenopus camello (SEQ ID NO:1), and FIG. 1B depicts the predicted amino acid sequence (SEQ ID NO:2) encoded by the nucleotide sequence of FIG. 1A.

Figures 2A, 2B:
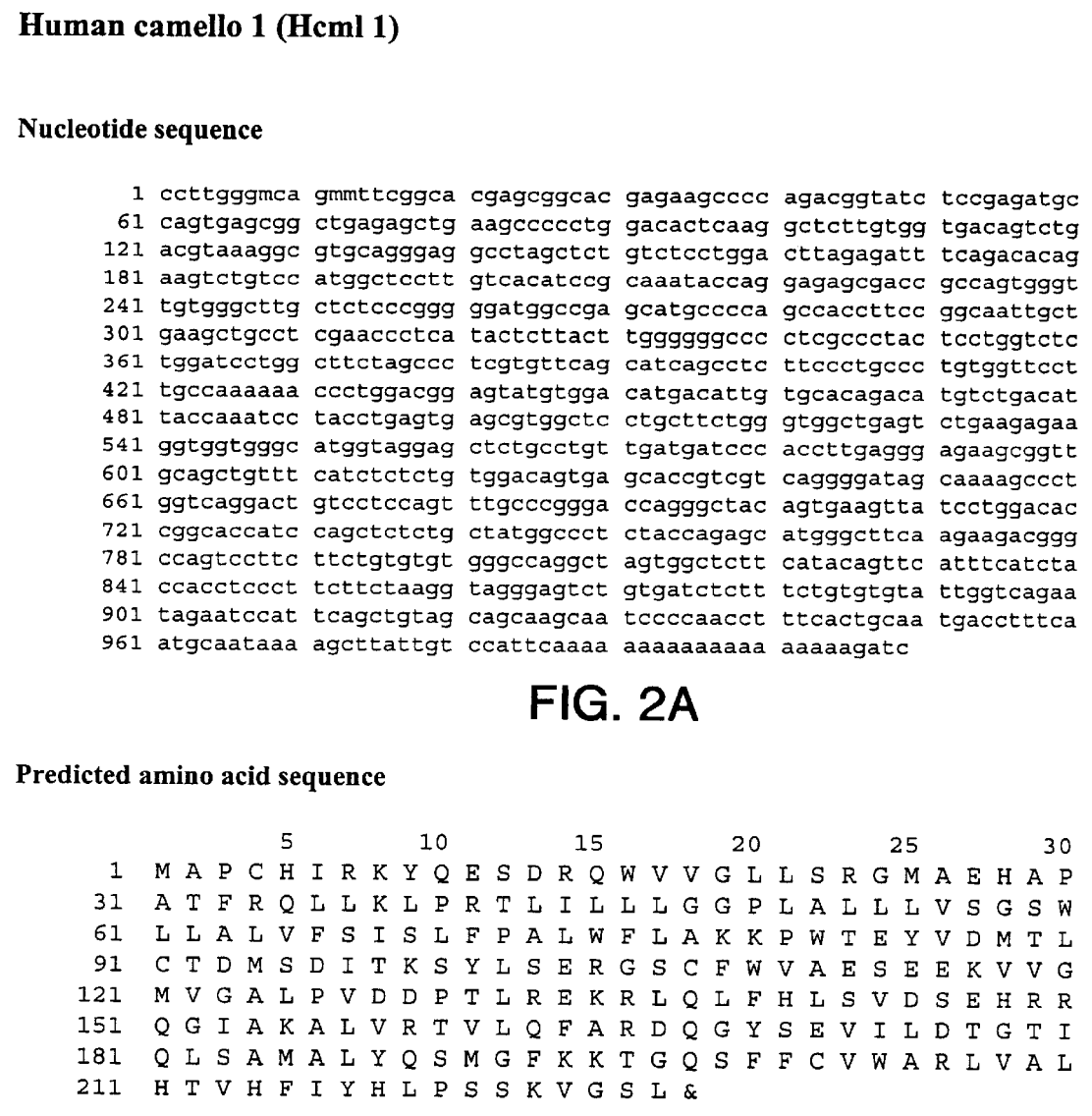

FIG. 2A depicts the nucleotide sequence of Human camello 1 (SEQ ID NO:3), and FIG. 2B depicts the predicted amino acid sequence (SEQ ID NO:4) encoded by the nucleotide sequence of FIG. 2A.

Figures 3A, 3B:
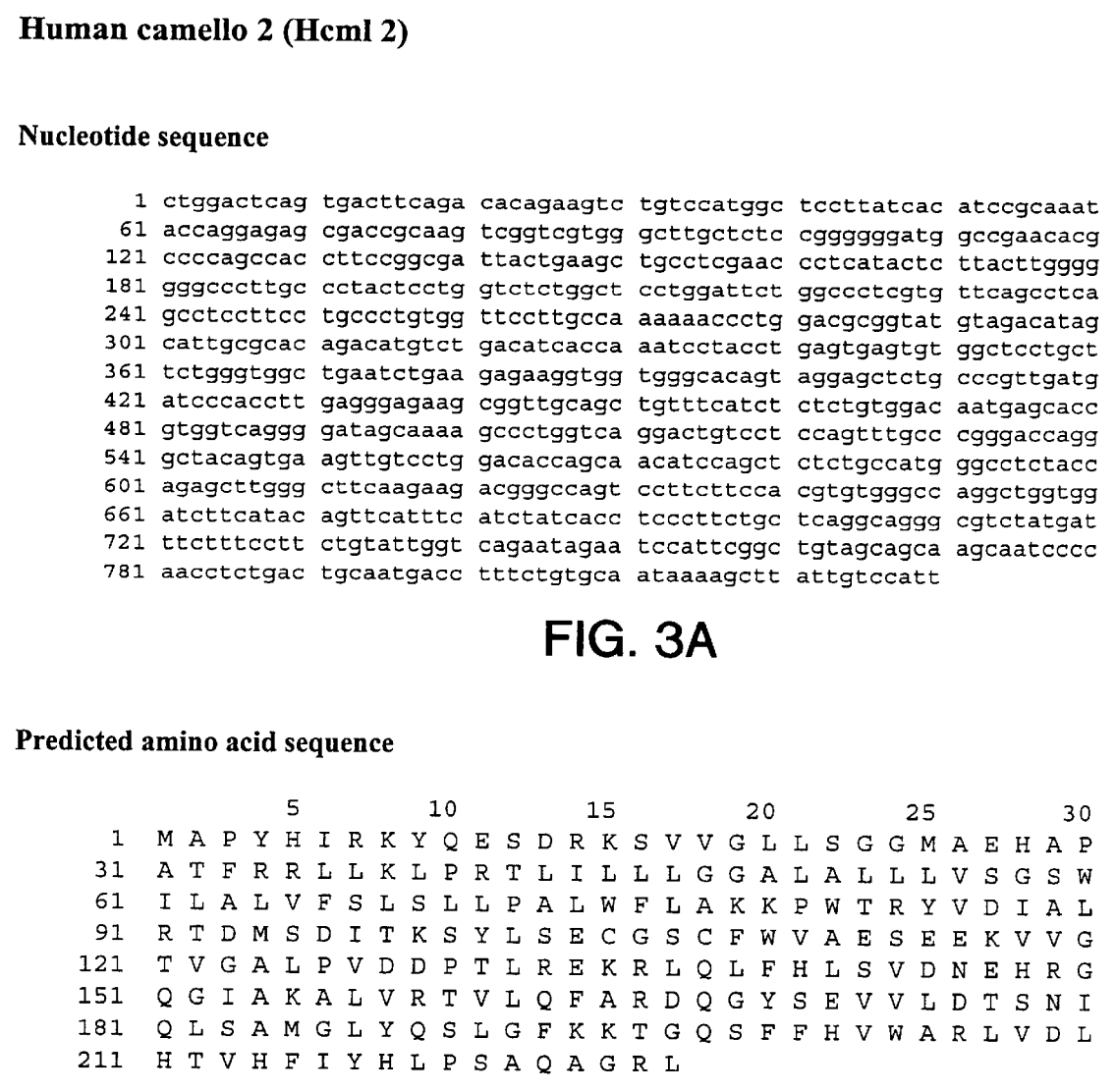

FIG. 3A depicts the nucleotide sequence of Human camello 2 (SEQ ID NO:5), and FIG. 3B depicts the predicted amino acid sequence (SEQ ID NO:6) encoded by the nucleotide sequence of FIG. 3A.

Figures 4A, 4B:
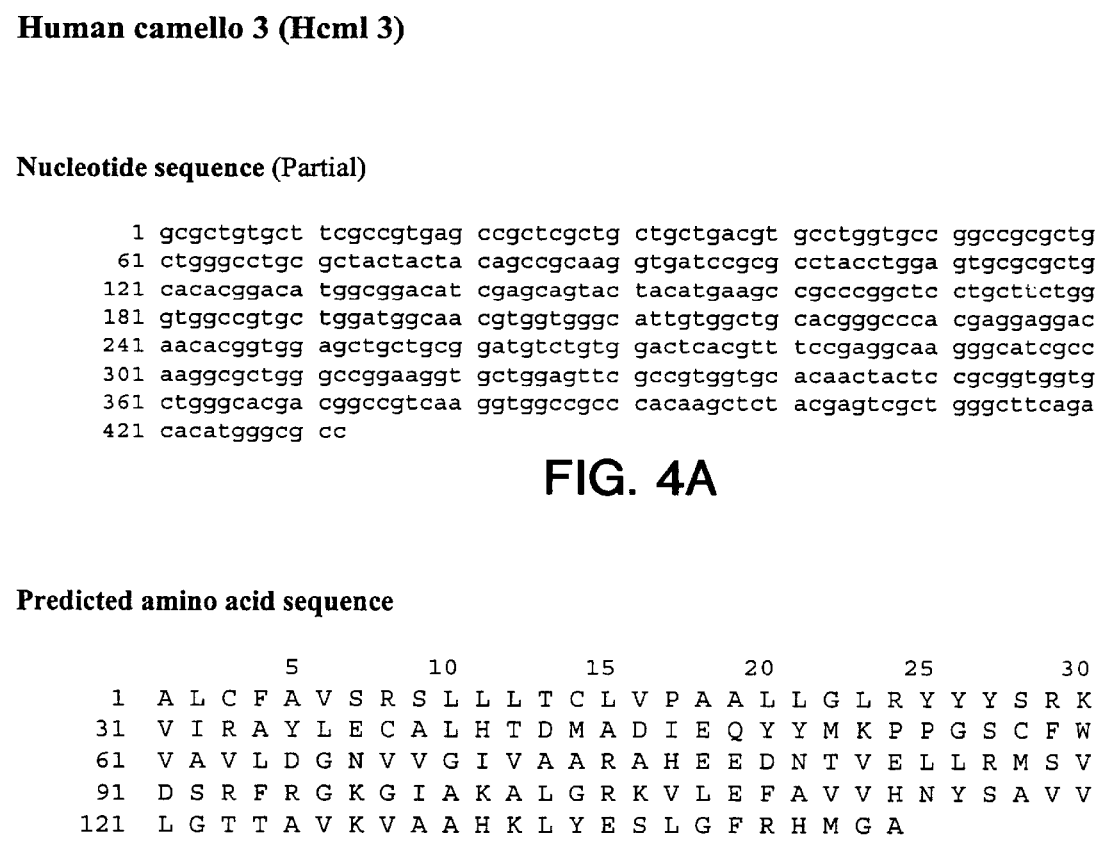

FIG. 4A depicts a partial nucleotide sequence of Human camello 3 (SEQ ID NO:7), and FIG. 4B depicts the predicted amino acid sequence (SEQ ID NO:8) encoded by the nucleotide sequence of FIG. 4A.

Figures 5A, 5B:
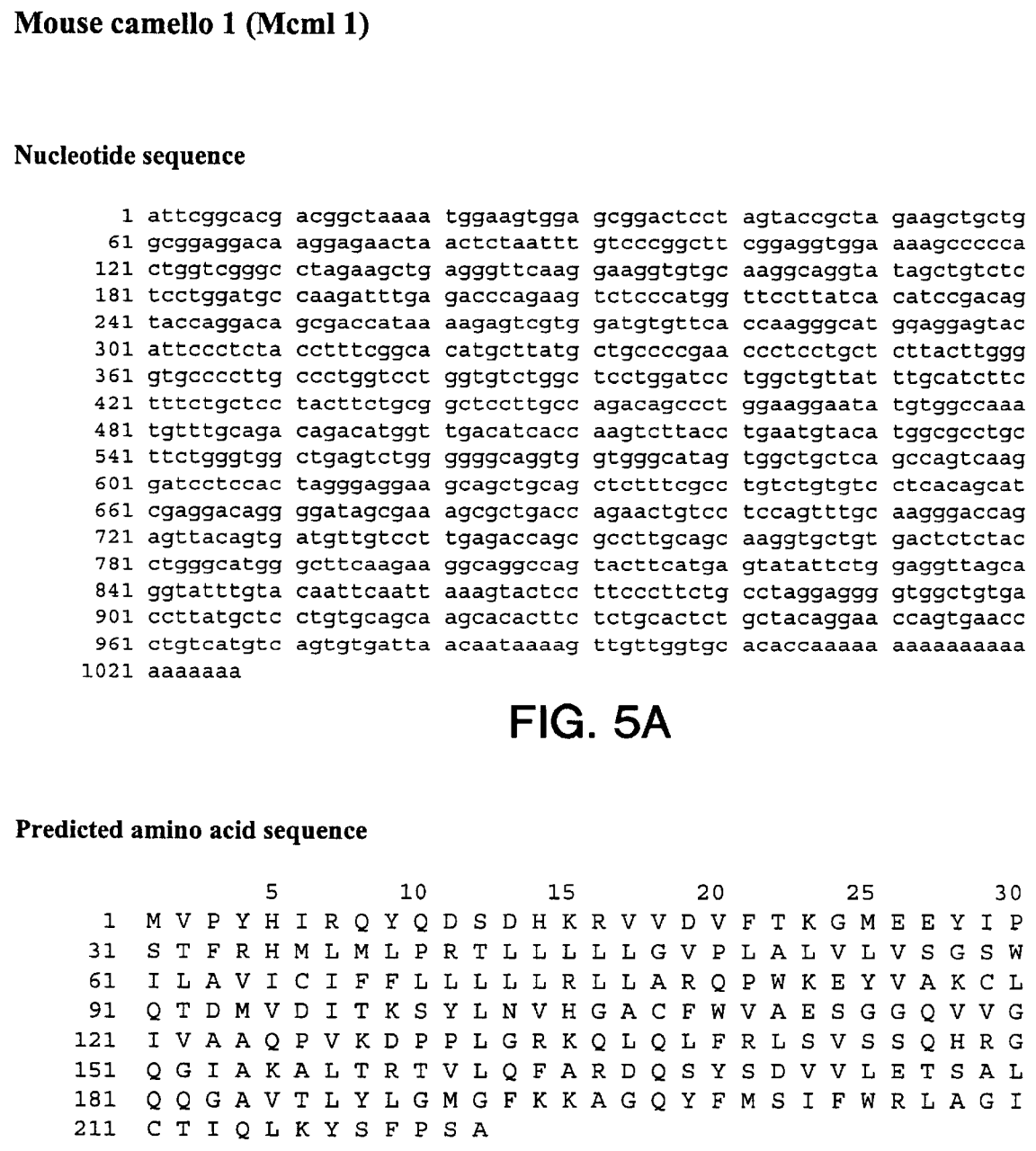

FIG. 5A depicts the nucleotide sequence of Mouse camello 1 (SEQ ID NO:9), and FIG. 5B depicts the predicted amino acid sequence (SEQ ID NO:10) encoded by the nucleotide sequence of FIG. 5A.

Figures 6A, 6B:
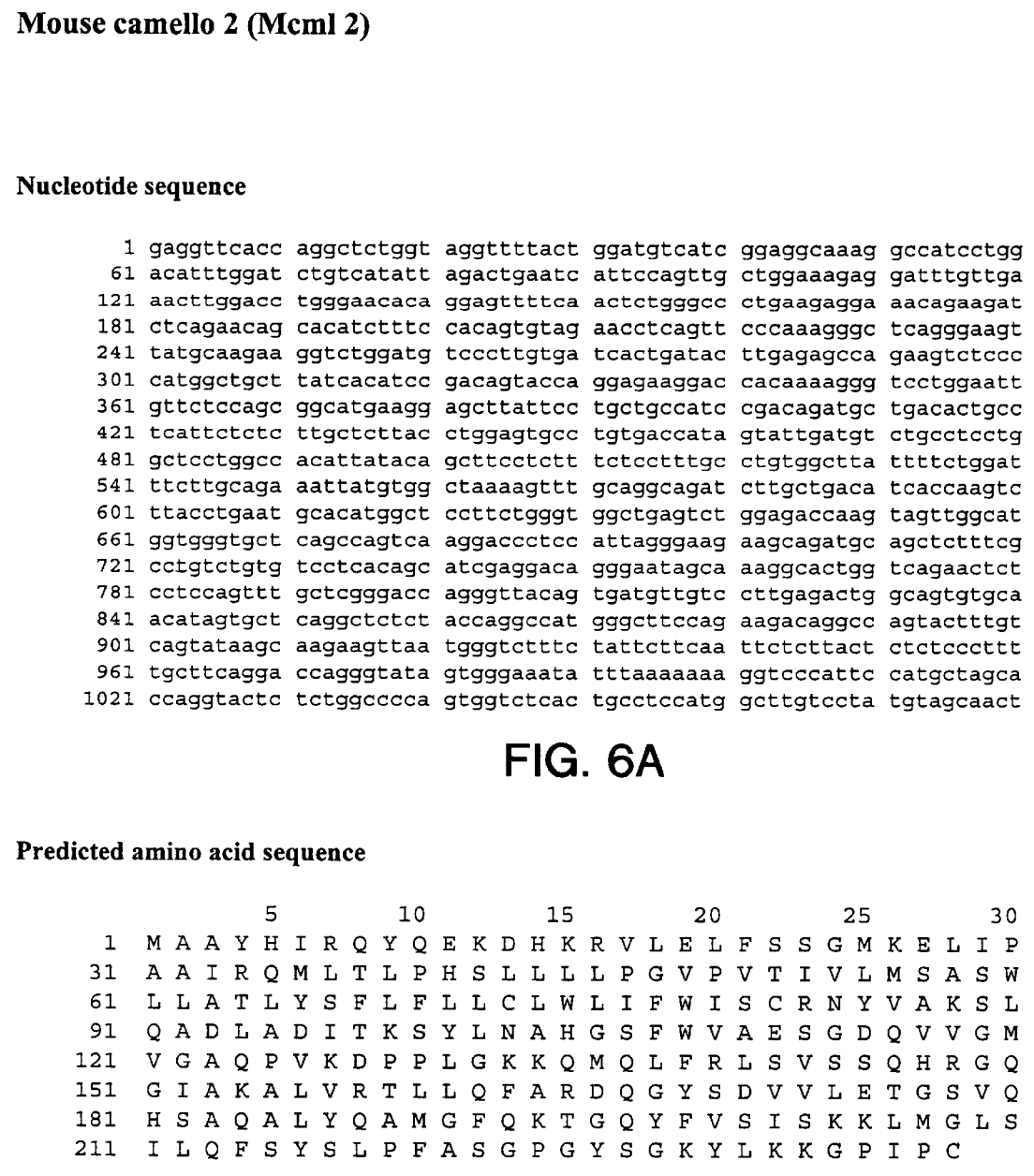

FIG. 6A depicts the nucleotide sequence of Mouse camello 2 (SEQ ID NO:11), and FIG. 6B depicts the predicted amino acid sequence (SEQ ID NO:12) encoded by the nucleotide sequence of FIG. 6A.

Figures 7A, 7B:
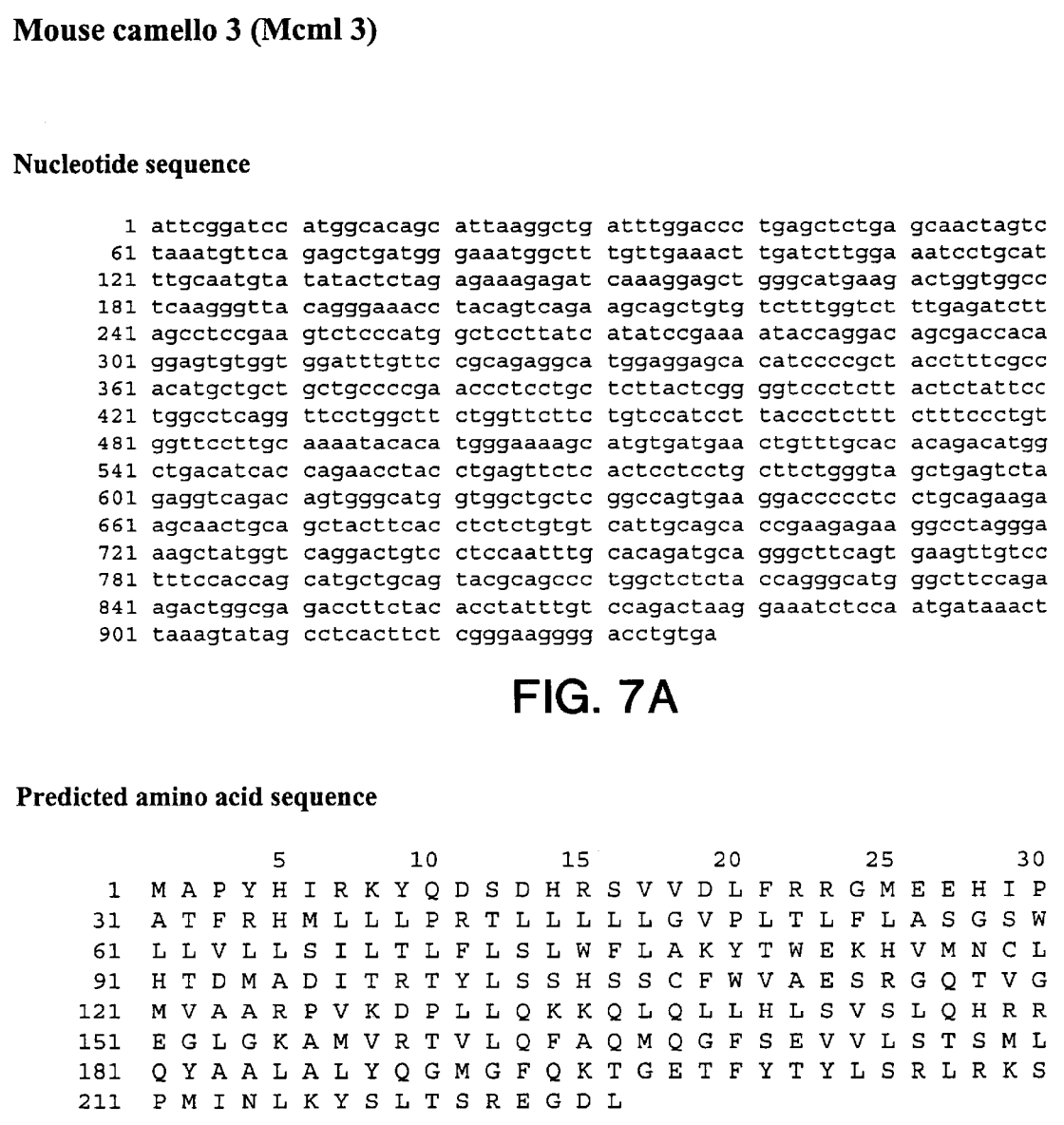

FIG. 7A depicts the nucleotide sequence of Mouse camello 3 (SEQ ID NO:13), and FIG. 7B depicts the predicted amino acid sequence (SEQ ID NO:14) encoded by the nucleotide sequence of FIG. 7A.

Figures 8A, 8B:
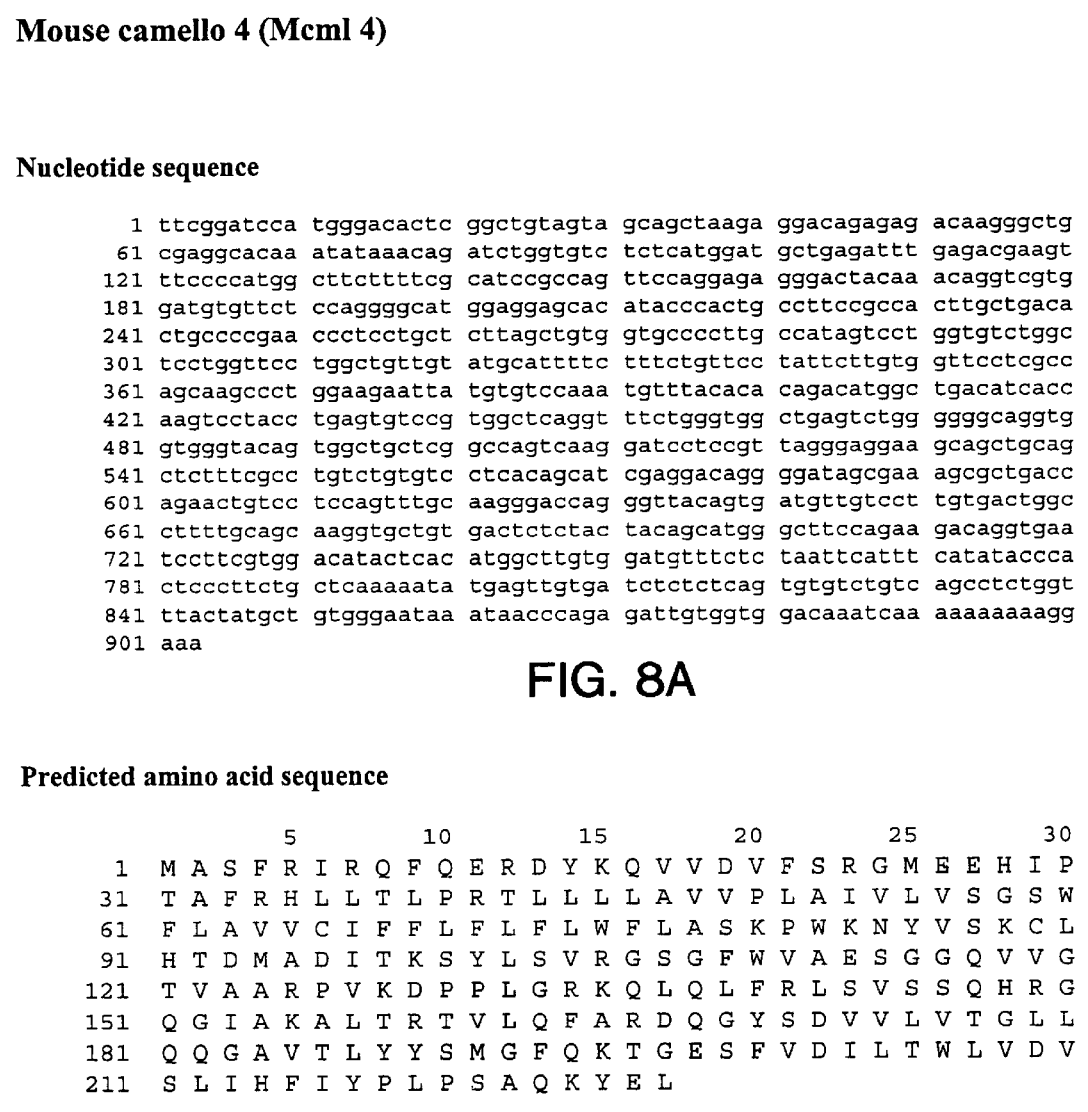

FIG. 8A depicts the nucleotide sequence of Mouse camello 4 (SEQ ID NO:15), and FIG. 8B depicts the predicted amino acid sequence (SEQ ID NO:16) encoded by the nucleotide sequence of FIG. 8A.

FIG. 9A depicts the partial nucleotide sequence of Mouse camello 5 (SEQ ID NO:17), and FIG. 9B depicts the predicted amino acid sequence (SEQ ID NO:18) encoded by the nucleotide sequence of FIG. 9A.

Figures 10A, 10B:
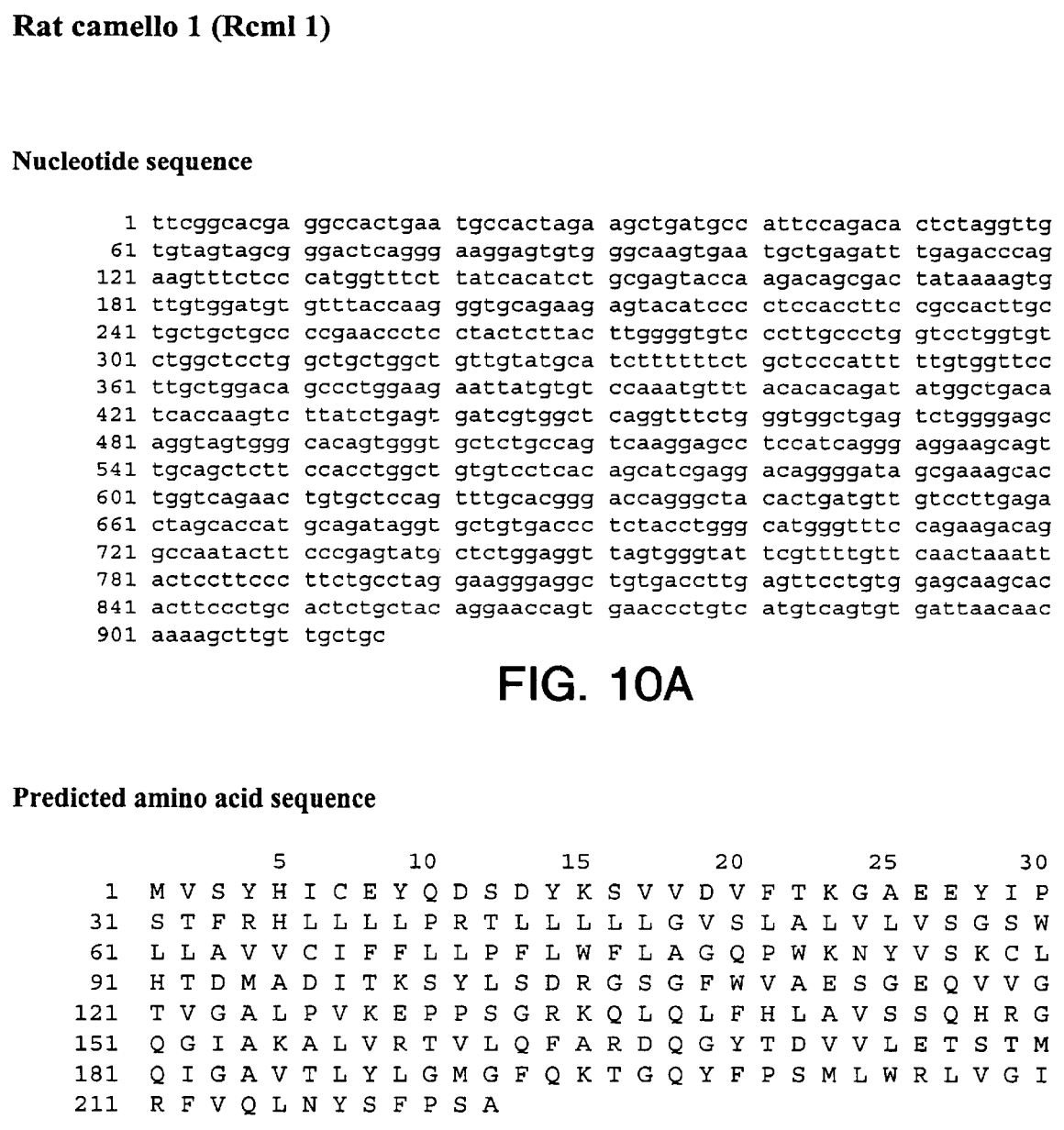

FIG. 10A depicts the nucleotide sequence of Rat camello 1 (SEQ ID NO:19), and FIG. 10B depicts the predicted amino acid sequence (SEQ ID NO:20) encoded by the nucleotide sequence of FIG. 10A.

Figures 11A, 11B:
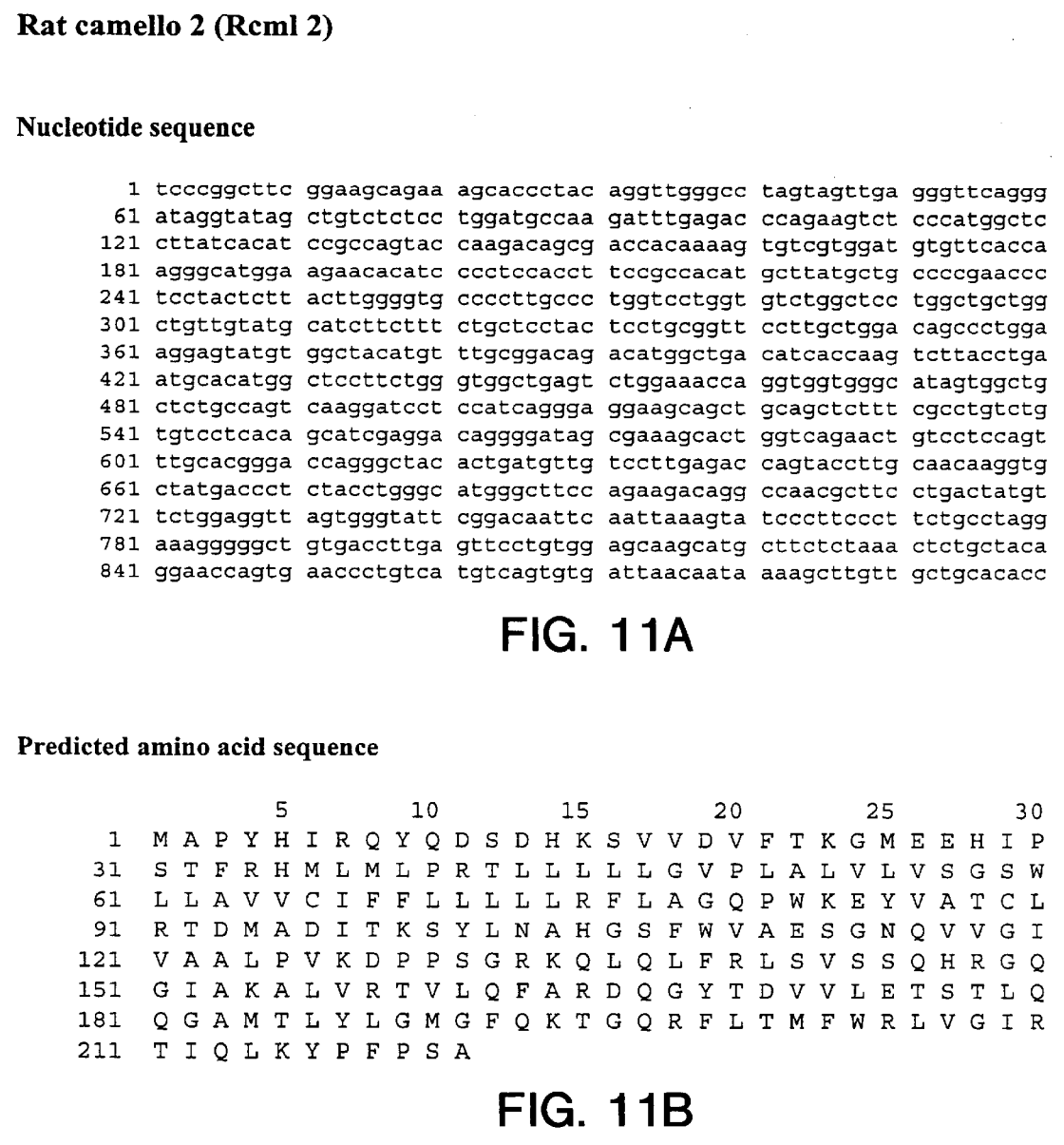

FIG. 11A depicts the nucleotide sequence of Rat camello 2 (SEQ ID NO:21), and FIG. 11B depicts the predicted amino acid sequence (SEQ ID NO:22) encoded by the nucleotide sequence of FIG. 11A.

Figures 12A, 12B:
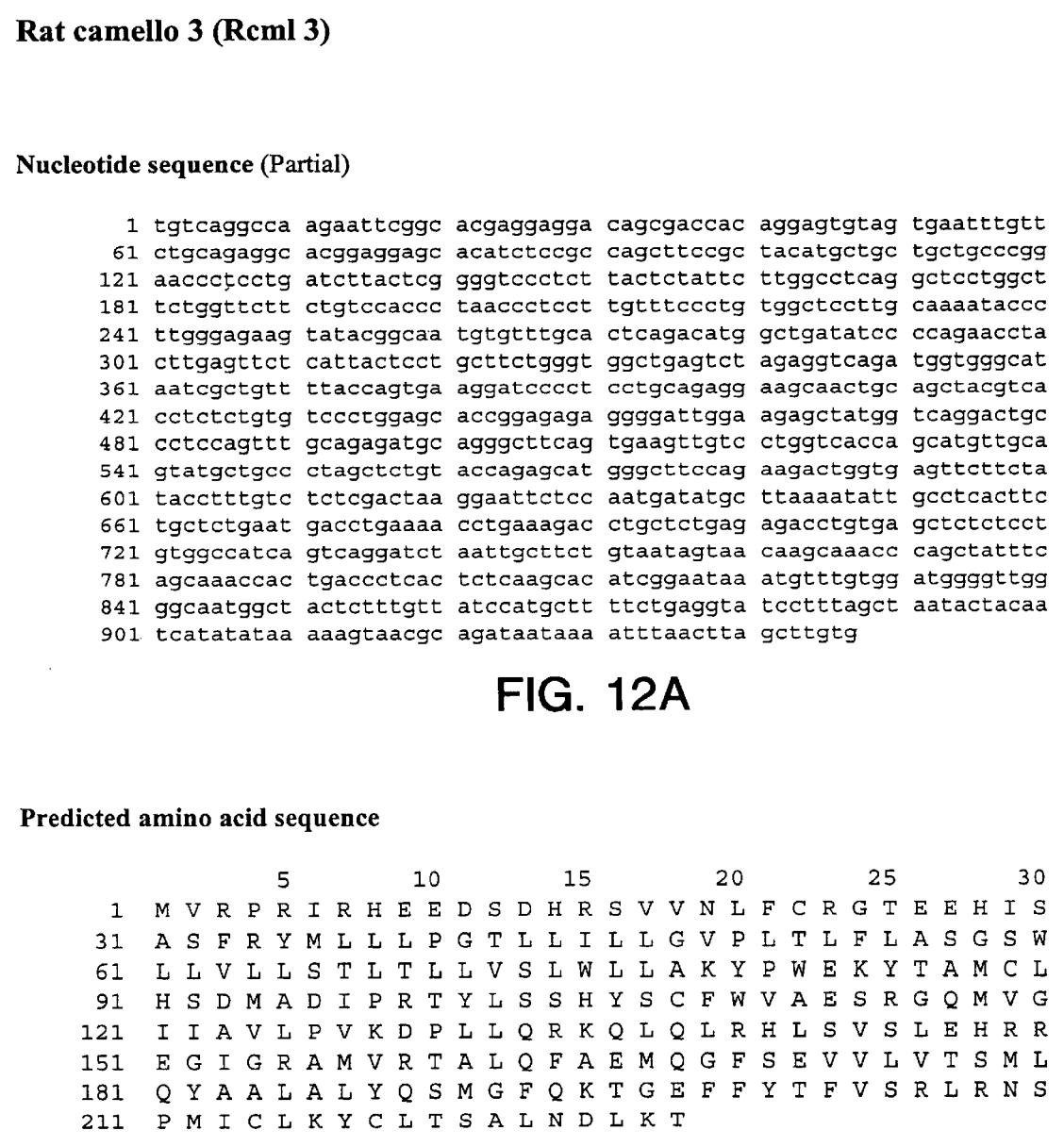

FIG. 12A depicts the partial nucleotide sequence of Rat camello 3 (SEQ ID NO:23), and FIG. 12B depicts the predicted amino acid sequence (SEQ ID NO:24) encoded by the nucleotide sequence of FIG. 12A.

Figures 13A, 13B:
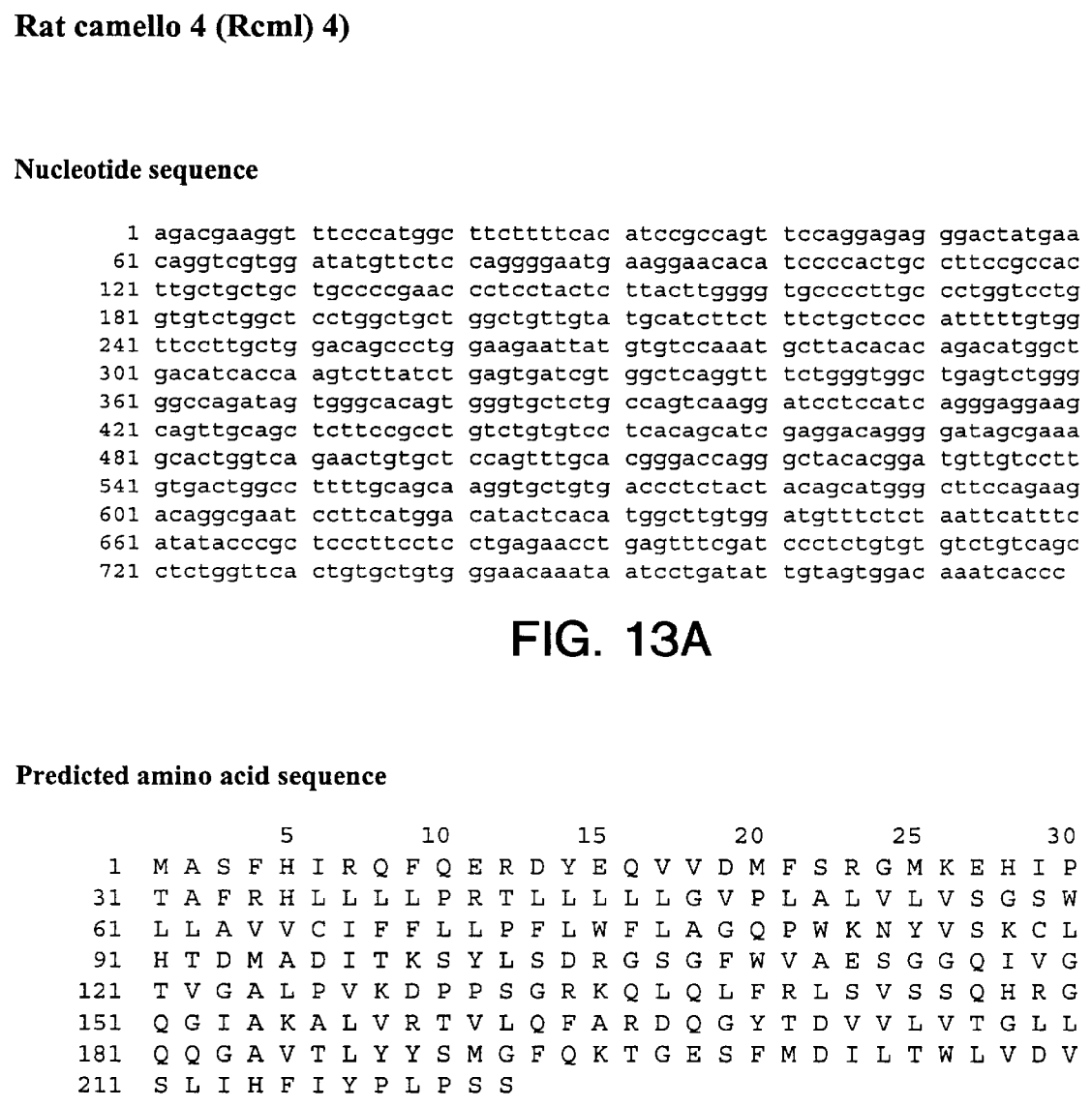

FIG. 13A depicts the nucleotide sequence of Rat camello 4 (SEQ ID NO:25), and FIG. 13B depicts the predicted amino acid sequence (SEQ ID NO:26) encoded by the nucleotide sequence of FIG. 13A.

FIG. 14 depicts the alignment of amino acid sequences (SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and SEQ ID NO: 26) of camello protein family members. There is a good match between camello consensus sequence and the characteristic motifs of N-acetyltransferase superfamily, positions of which are indicated. The position of the hydrophobic domain is also indicated.

FIG. 18 depicts Xcml protein localized in the organelles of the secretory pathway. (a–c) subcellular localization of Xcml-GFP fusion protein in COS-7 cells studied by confocal microscopy. (a) distribution GFP signal in COS-7 cells; (b) same as a, but cells were additionally stained with BODIPY TR ceramide, Golgi marker; simultaneous detection of GFP (green) and ceramide (red) signals. (c) COS-7 cells transfected with XcmlDF42L80-GFP construct and stained with BODIPY TR ceramide with simultaneous detection of both signals. (d) COS-1 cells transfected with Xcml-GFP stained with Hoechst that marks nucleus. (e) western blot analysis of Xenopus oocytes injected with C- and N-terminal myc-tagged Xcml and myc-tagged Sizzled as a positive control; M, culture medium; V, vesicular fraction; C, cytoplasmic fraction.

DETAILED DESCRIPTION OF THE INVENTION

Figure 15A:
FIG. 15 depicts the expression of Xcml during Xenopus development. (a) temporal expression of Xcml mRNA studied by Northern blot analysis, developmental stages are indicated on top. Molecular-size marker is shown at the right. (b–h) spatial pattern of Xcml mRNA expression studied by whole mount in situ hybridization; (dl) dorsal lip; (vl) ventral lip. Expression is first detectable in the periblastoporal region at the onset of gastrulation, stage 10,5(b); expression is stronger in the marginal zone at stages 11(c) and 12(d). This pattern is preserved until the neurula stage 16(e). Sagittal sections of Xcml stained Xenopus embryos demonstrate expression of Xcml in deep cells of marginal zone at the beginning of gastrulation movements, stage 10,5(f) and in the region of contact non-involuted and involuted cells at stage 12(g). Expression is absent in more deep layers of presumptive mesoderm (g, h), in the cells of outer surface and surface of archenteron (arh); (h) dorsal lip with high magnification.

The present invention provides a purified and isolated nucleic acid encoding a camello protein. As used herein, the nucleic acid may be genomic DNA, cDNA, RNA or antisense RNA and includes nucleic acid derived from any species, e.g., human, rat, goat, pig, mouse, frog and cow. Due to the degeneracy of the genetic code, the nucleic acid of the present invention also includes a multitude of nucleic acid substitutions which will encode camello. The nucleic acid from the frog preferably encodes the amino acid sequence for Xenopus camello (Xcml) as shown in FIG. 1B, and more preferably comprises the nucleotide sequence as shown in FIG. 1A. The nucleic acid from a human preferably encodes the amino acid sequences for human camello shown in FIG. 2B (Hcml1), 3B (Hcml2) or 4B (Hcml3), and more preferably comprises the nucleotide sequence shown in FIG. 2A, 3A or 4A, respectively. The nucleic acid from the mouse preferably encodes for the amino acid sequences for mouse camello as shown in FIG. 5B (Mcml1), 6B (Mcml2), 7B (Mcml3), 8B (Mcml4) or 9B (Mcml5), and more preferably comprises the nucleotide sequence shown in FIG. 5A, 6A, 7A, 8A or 9A, respectively. The nucleic acid for the rat preferably encodes for the amino acid sequences for rat camello as shown in FIG. 10B (Rcml1), 11B (Rcml2), 12B (Rcml3) or 13B (Rcml4), and more preferably comprises the nucleotide sequence set forth in FIG. 10A, 11A, 12A, or 13A, respectively.

The present invention also includes nucleic acid sequences that are at least 80%, preferably at least 85%, more preferably at least 90%, and most preferably at least 95%, homologous with each of the nucleic acid sequences set forth above. In addition, the present invention provides the nucleic acid encoding the camello protein having one or more mutations resulting in the expression of a non-functional or mutant protein, or in lack of expression altogether. The mutation may be one or more point, insertion, rearrangement or deletion mutations or a combination thereof.

The present invention further provides a vector which comprises nucleic acid encoding a camello protein. Such vectors may be constructed by inserting nucleic acid encoding camello into suitable vector nucleic acid. The term "inserted" as used herein means the ligation of a foreign DNA fragment and vector DNA by techniques such as the annealing of compatible cohesive ends generated by restriction endonuclease digestion or by use of blunt end ligation techniques. Other methods of ligating DNA molecules will be apparent to one skilled in the art. Vectors may be derived from a number of different sources. They can be plasmids, viral-derived nucleic acids, lytic bacteriophage derived from phage lambda, cosmids or filamentous single-stranded bacteriophages such as M13. Depending upon the type of host cell into which the vector is introduced, vectors may be bacterial or eukaryotic. Bacterial vectors are derived from many sources including the genomes of plasmids and phage. Eukaryotic vectors are also constructed from a number of different sources, e.g., yeast plasmids and viruses. Some vectors, called shuttle vectors, are capable of replicating in both bacteria and eukaryotes. The nucleic acid from which the vector is derived is usually greatly reduced in size so that only those genes essential for its autonomous replication remain. The reduction in size enables the vectors to accommodate large segments of foreign DNA. Examples of suitable vectors into which the nucleic acid encoding the camello protein can be inserted include but are not limited to pBR322, pUC18, pUC19, pHSV-106, pJS97, pJS98, M13mp18, M13mp19, pSPORT 1, pGem, pSPORT 2, pSV.SPORT 1, pBluescript II, λZapII, λgt10, λgt11, λgt22A, and λZIPLOX. Other suitable vectors are obvious to one skilled in the art.

The vector of the present invention may be introduced into a host cell and may exist in integrated or unintegrated form within the host cell. When in unintegrated form, the vector is capable of autonomous replication. The term "host cell" as used herein means the bacterial or eukaryotic cell into which the vector is introduced. As used herein, "introduced" is a general term indicating that one of a variety of means has been used to allow the vector to enter the intracellular environment of the host cell in such a way that it exists in stable and expressable form therein.

Some bacterial and eukaryotic vectors have been engineered so that they are capable of expressing inserted nucleic acids to high levels within the host cell. Such vectors utilize one of a number of powerful promoters to direct the high level of expression. For example, in vectors for the expression of a gene in a bacterial host cell such as E. coli, the lac operator-promoter or the tac promoter are often used. Eukaryotic vectors use promoter-enhancer sequences of viral genes, especially those of tumor viruses. Expression can be controlled in both bacterial and eukaryotic cells using inducible promoters such as the lac operator-promoter in E. coli or metallothionine or mouse mammary tumor virus promoters in eukaryotic cells. As used herein, "expression" refers to the ability of the vector to transcribe the inserted nucleic acid into mRNA so that synthesis of the protein encoded by the inserted nucleic acid can occur.

Vectors suitable for the expression of the nucleic acid encoding camello in a host cell are well known to one skilled in the art and include pET-3d (Novagen), PROEX™ HT Prokaryotic Expression System (Life Technologies), Plasmid pFASTBAC™1 Expression Vector (Life Technologies), pSFV (Life Technologies), pSFV (Life Technologies), pcDNA II (Invitrogen), pSL301 (Invitrogen), pSE280 (Invitrogen), pSE380 (Invitrogen), pSE420 (Invitrogen), pTrcHis A,B,C (Invitrogen), pRSET A,B,C (Invitrogen), pYES2 (Invitrogen), pAC360 (Invitrogen), pVL1392 and pVl1392 (Invitrogen), pCDM8 (Invitrogen), pcDNA I (Invitrogen), pcDNA I(amp) (Invitrogen), pZeoSV (Invitrogen); pcDNA 3 (Invitrogen), pRc/CMV (Invitrogen), pRc/RSV (Invitrogen), pREP4 (Invitrogen), pREP7 (Invitrogen), pREP8 (Invitrogen), pREP9 (Invitrogen), pREP10 (Invitrogen), pCEP4 (Invitrogen), pEBVHis (Invitrogen), and λPop6. Other vectors would be apparent to one skilled in the art.

Vectors maybe introduced into host cells by a number of techniques known to those skilled in the art, e.g., electroporation, DEAE dextran, cationic liposome fusion, protoplast fusion, DNA coated-microprojectile bombardment, and infection with recombinant replication-defective retroviruses. The term "transformation" denotes the introduction of a vector into a bacterial or eukaryotic host cell. As such, it encompasses transformation of bacterial cells and transfection, transduction and related methods in eukaryotic cells.

Any one of a number of suitable bacterial or eukaryotic host cells may be transformed with the vector of the present invention. Examples of suitable host cells are known to one skilled in the art and include but are not limited to bacterial cells such as E. coli strains c600, c600hfl, HB101, LE392, Y1090, JM103, JM109, JM101, JM107, Y1088, Y1089, Y1090, Y1090(ZZ), DM1, PH10B, DH11S, DH125, RR1, TB1 and SURE, Bacillus subtilis, Agrobacterium tumefaciens, Bacillus megaterium; and eukaryotic cells such as Pichia pastoris, Chlamydomonas reinhardtii, Cryptococcus neoformans, Neurospora crassa, Podospora anserina, Saccharomyces cerevisiae, Saccharomyces pombe, Uncinula necator, cultured insect cells, cultured chicken fibroblasts, cultured hamster cells, cultured human cells such as HT1080, MCF7, 143B and cultured mouse cells such as EL4 and NIH3T3 cells.

The present invention also provides a method for producing a recombinant camello protein comprising growing a host cell transformed with a vector encoding camello in culture and recovering recombinant camello. As used herein the term "recombinant" refers to camello produced by purification from a host cell transformed with a vector capable of directing its expression to a high level. A variety of methods of growing host cells transformed with a vector are known to those skilled in the art. The type of host cell, i.e., whether the host cell is bacterial or eukaryote, is the primary determinant of the method to be utilized and the optimization of specific parameters relating to such factors as temperature, trace nutrients, humidity, and growth time. Depending on the vector, the host cells may have to be induced by the addition of a specific compound at a certain point in their growth cycle in order to initiate expression of the nucleic acid of the present invention. Examples of compounds used to induce expression of the nucleic acid of the present invention are known to one skilled in the art and include but are not limited to IPTG, zinc and dexamethasone. Using standard methods of protein isolation and purification, such as ammonium sulfate precipitation followed by dialysis to remove salt, followed by fractionation according to size, charge of the protein at specific pH values, affinity methods, etc., recombinant camello may be extracted from suitable host cells transformed with vector capable of expressing the nucleic acid encoding camello.

The present invention also provides a purified camello protein and analogues thereof and includes camello isolated from tissue obtained from a subject or recombinantly produced as described above. As used herein "analogues" may be any protein having functional similarity to the camello protein, that also possesses certain regions that are conserved among the Camello family members (e.g., the central hydrophobic domain). Preferably, the camello protein from the frog preferably comprises the amino acid sequence for Xenopus camello (Xcml) as shown in FIG. 1B. Preferably, the camello protein from the human comprises the amino acid sequences shown in FIG. 2B (Hcml1), 3B (Hcml2) or 4B (Hcml3). The camello protein for the mouse preferably comprises the amino acid sequences as shown in FIG. 5B (Mcml1), 6B (Mcml2), 7B (Mcml3), 8B (Mcml4) or 9B (Mcml5. The camello protein for the rat preferably comprises the amino acid sequences shown in FIG. 10B (Rcml1), 11B (Rcml2), 12B (Rcml3) or 13B (Rcml4). The camello protein also includes amino acid sequences that are at least 70%, preferably at least 75%, more preferably at least 80%, and most preferably at least 90% homologous with each of the amino acid sequences set forth above. The present invention also includes a non-functional camello protein, i.e., camello which is inactive or only has minimal effects in vivo. The non-functional camello protein may have one or more deletions or substitutions of its amino acid sequence that results in the camello protein losing its functionality.

The present invention also provides for agents that bind to the camello protein and analogues thereof, as well as the non-functional camello protein. The agent may be a antibody, a nucleic acid, a protein, a peptide, DNA, RNA, mRNA, antisense RNA, a drug or a compound. Agents that bind to the camello protein or an analogue thereof may be identified or screened by contacting the protein with the agent of interest and assessing the ability of the agent to bind to the protein. Agents that bind to the camello protein may act to inhibit metastasis by inhibiting the anti-adhesion effects of camello expression and, therefore, may be useful as chemotherapeutic agents for cancer and tumor treatment. Such agents also may be useful for the treatment or prevention of birth defects.

Antibodies immunoreactive with camello or analogues thereof include antibodies immunoreactive with non-functional camello protein. The antibodies of the present invention may be monoclonal or polyclonal and are produced by techniques well known to those skilled in the art, e.g., polyclonal antibody can be produced by immunizing a rabbit, mouse, or rat with purified camello and monoclonal antibody may be produced by removing the spleen from the immunized rabbit, mouse or rat and fusing the spleen cells with myeloma cells to form a hybridoma which, when grown in culture, will produce a monoclonal antibody. Labeling of the antibodies of the present invention may be accomplished by standard techniques using one of the variety of different chemiluminescent and radioactive labels known in the art. The antibodies of the present invention may also be incorporated into kits which include an appropriate labeling system, buffers and other necessary reagents for use in a variety of detection and diagnostic applications.

The present invention provides for agents that bind to a nucleic acid encoding camello protein. Suitable agents include but are not limited to a nucleic acid, a protein, a peptide, DNA, RNA, mRNA, antisense RNA, a drug or a compound. Preferably, the agents inhibit expression of the camello nucleic acid. Such agents may be discovered by a method for screening for an agent that binds to the nucleic acid of camello comprising contacting the nucleic acid with an agent of interest and assessing the ability of the agent to bind to the nucleic acid. An agent that inhibits the expression of the nucleic acid encoding the camello protein may be screened by contacting a cell transformed with a vector comprising the nucleic acid, and assessing the effect of the agent on expression of the nucleic acid. Agents that bind to the nucleic acid encoding camello may act to inhibit metastasis of tumors by inhibiting the anti-adhesion effects of camello expression.

The present invention also provides nucleic acid probes and mixtures thereof which are hybridizable to the nucleic acid encoding the camello protein. Such probes may be prepared by a variety of techniques known to those skilled in the art such as PCR and restriction enzyme digestion of camello nucleic acid or by automated synthesis of oligonucleotides whose sequences correspond to selected portions of the nucleotide sequence of the camello nucleic acid using commercially available oligonucleotide synthesizers such as the Applied Biosystems Model 392 DNA/RNA synthesizer. The nucleic acid probes of the present invention may also be prepared so that they contain one or more point, insertion, rearrangement or deletion mutations or a combination thereof to correspond to mutations of the camello gene. The nucleic acid probes of the present invention may be DNA or RNA and may vary in length from about 8 nucleotides to the entire length of the camello nucleic acid. Preferably, the probes are 8 to 30 nucleotides in length. Labeling of the nucleic acid probes may be accomplished using one of a number of methods known in the art, e.g., PCR, nick translation, end labeling, fill-in end labeling, polynucleotide kinase exchange reaction, random priming, or SP6 polymerase (for riboprobe preparation) and one of a variety of labels, e.g., radioactive labels such as $^{35}$S, $^{32}$P, or $^3$H or nonradioactive labels such as biotin, fluorescein (FITC), acridine, cholesterol, or carboxy-X-rhodamine (ROX). Combinations of two or more nucleic probes corresponding to different or overlapping regions of the camello nucleic acid may also be included in kits for use in a variety of detection and diagnostic applications.

The present invention also provides a method for diagnosing developmental defects in an embryo or fetus associated with abnormal expression in the subject's cells. Abnormal expression of camello may be associated with defects in gastrulation. Gestational defects in an embryo or fetus resulting from an increased or decreased expression of camello may be diagnosed by nucleic acid hybridization and/or immunological techniques well known in the art. For example, nucleic acid hybridization using mRNA extracted from cells and camello nucleic acid probes can be used to determine the concentration of camello mRNA present in the cell and the concentration thus obtained compared to the value obtained for cells which exhibit a normal level of camello activity. Isolation of RNA from cells is well known in the art and may be accomplished by a number of techniques, e.g., whole cell RNA can be extracted using guanidine thiocyanate; cytoplasmic RNA may be prepared by using phenol extraction methods; and polyadenylated RNA may be selected using oligo-dT cellulose. Alternatively, the concentration of camello in the cell may be determined from binding studies using antibody immunoreactive with camello. Gestational defects resulting from mutations in the nucleic acid encoding camello may be detected by one of a number of methods known in the art, e.g., hybridization analysis of nucleic acid extracted from a sample of tissue or cells from a subject using nucleic acid probes designed to detect the presence of mutations in the nucleic acid encoding camello. Alternatively, the defect may be detected using antibody immunoreactive with non-functional camello and standard immunological detection techniques such as Western blotting.

Increased expression of camello in cancer or tumor cells, which may be indicative of increased metastasis or aggressiveness of the tumor, may be detected by nucleic acid hybridization and/or immunological techniques well known in the art. For example, nucleic acid hybridization using mRNA extracted from cells and camello nucleic acid probes can be used to determine the concentration of camello mRNA present in the cell and the concentration thus obtained compared to the value obtained for cells which exhibit a normal level of camello activity. Alternatively, the concentration of camello in the cell may be determined from binding studies using antibody immunoreactive with camello.

Finally, the method of the present invention also provides a non-human animal model for the study of camello expression. The animal model of the present invention comprises a non-human, transgenic animal having nucleic acid encoding the camello protein incorporated into at least some of the somatic cells of the animal. The effect of the expression of the camello protein also may be studied by overexpressing or underexpressing the protein using suitable promoters and regulators known in the art. It is also within the confines of the present invention that a nucleic acid sequence having one or more mutations may be introduced into the animal model that result in the expression of a non-functional or mutant protein. Nucleic acid encoding mutated camello may be integrated into the germ line of a non-human animal such as a mouse, rat, goat, sheep, or other species in order to obtain a transgenic animal. Expression of the incorporated nucleic acid may be restricted to certain tissues in the transgenic animal by the utilization of tissue-specific promoters. Methods of making transgenic animals are well known in the art. For example, DNA encoding mutated camello can be inserted into the genome of a replication-defective virus such as HSV, or a retrovirus or transposon, and the resultant construct injected into embryonic stem cells. Transgenic animals may also be made by injecting DNA encoding mutated camello into the male pronucleus of a fertilized egg of a nonhuman animal, transplanting the "transgenic embryo" into a pseudopregnant female and then analyzing offspring for the presence of the injected DNA in their genome. Other methods of producing transgenic mice would be apparent to one skilled in the art.

The present invention is described in the following Experimental Details Section which is set forth to aid in the understanding of the invention, and should not be construed to limit in any way the invention as defined in the claims which follow thereafter.

EXPERIMENTAL DETAILS SECTION

1. Materials and Methods

Molecular Analysis of Xcml and Mammalian Camello Family Members

N4 Xcml cDNA fragment, isolated using Gene Expression Fingerprinting procedure, was used as a probe for screening *Xenopus laevis* stage 10,5 embryo cDNA library. pBluescript SK(-) plasmids were excised from positive clones using R408 helper phage, and the largest clone 1,2 kb long was sequenced in both directions. EST clones containing murine, rat and human camello family sequences were obtained from Genome Systems, Inc. (St. Louis, Mo.) and ATCC and sequenced using flanking and gene-specific primers.

Plasmid Constructs and Site-directed Mutagenesis

For microinjection experiments the Xcml open reading frame was PCR amplified with Advantage cDNA polymerase mix and inserted into BamH1/Xba1-cleaved pCS2+ vector. Xcml constructs fused- or C-terminally with six tandemly-repeated copies of myc epitope (myc-tag) were produced by in-frame insertion of PCR amplified Xcml open reading frame into Xho1/Xba1- or BamH1-digested pCS2+ MT vector. For Xcml constructs C-terminally fused with Green Flourescent Protein PCR fragments containing intact protein coding sequence or sequence with deletion of hydrophobic domains were cloned in-frame into Xho1-BamH1 sites of pEGFP-N1 vector (Clontech).

Constructs of mutated Xcml protein were created using site-directed mutagenesis by inverse PCR. Xcml-pCS2+ circular plasmid nicked by DNAse I as described was used as a template. Amplifications were carried out using the Advantage cDNA PCR kit (Clontech) for 10 cycles (95° C., 30 seconds; 60° C., 30 seconds; 68° C., 4 minutes). The amplified fragments were gel purified and self-ligated. XcmlA31F mutant contained a frameshift after Ala31 and a translation stop five amino acids further downstream. XcmlA32S and XcmlQ147S had stop-codons after Ala32 and Gln147, respectively. In the XcmlDF42L80 mutant an internal hydrophobic domain between Arg41 and Glu81 was deleted. All constructs and mutants were checked by sequencing.

Northern Blot Analysis

Isolation of total and poly(A)$^+$ RNA from embryos were performed as described. For Northern analysis poly(A)$^+$ RNA was separated in a 1.2% formaldehyde-agarose gel and transferred by capillary blotting onto Hybond-N nylon membrane according to manufacturer instructions. Blot was probed with [$^{32}$P]dATP-labeled Xcml and washed in stringent conditions.

In situ Hybridization

Whole-mount in situ hybridization was performed according to Harland (1991) using digoxigenin-labeled antisense RNA probes synthesized from Xcml plasmids using T7 RNA polymerase.

RNA Synthesis and Microinjection

Synthetic capped sense mRNAs were produced using the Ambion Message Machine SP6 kit using corresponding linearized plasmids. Xenopus embryos were obtained by in vitro fertilization, chemically degelled with 2% cysteine hydrochloride (pH 8.0) at the 2-cell stage, washed with 0.1×MMR (1×MMR: 100 mM NaCl, 2 mM KCl, 1 mM $MgSO_4$, 2 mM $CaCl_2$, 5 mM Hepes, pH 7.6, 0.1 mM EDTA) and transferred to ⅓×MMR supplemented with 4% Ficoll type 400 (Sigma). Capped mRNA in 4.6 nl of RNAse-free water was injected in embryos at the 8-cell stage. At the mid-blastula stage embryos were placed in 0.1×MMR. Staging was performed according to Nieuwkoop and Faber (1975).

Western Blot Analysis

Manually defolliculated oocytes were injected in OR2 medium (82.5 mM NaCl, 2.5 mM KCl, 1 mM $CaCl_2$, 1 mM $MgCl_2$, 1 mM $Na_2HPO_4$, 5 mM HEPES, pH 7.6) with 30 ng of mRNA in 28 nl of water and cultured overnight at room temperature in 0.5×MMR, 0.5 mg/ml BSA, 50 units/ml penicillin, 50 mg/ml streptomycin (10 ml per oocyte). Culture medium was collected and acetone-precipitated. Oocytes were fractionated into cytosolic and vesicle fractions. Proteins (20 mg per lane) were separated by SDS-PAGE, transferred to nitrocellulose membrane by electroblotting and probed with rabbit antibodies against myc-tag followed by goat anti-rabbit IgG secondary antibodies conjugated with horseradish peroxidase (Amersham). The protein bands were visualized using enhanced chemiluminescence.

Cell Culture

For cell-localization findings COS-1 cells were transfected with 10 mg of Xcml-pEGFP-N1 plasmid or pEGFP-N1 using the calcium phosphate technique (Graham and Van Der Eb, 1973) and cultured up to 3 days in DMEM with 10% FBS medium. For nuclear staining 0.25 mg/ml of Hoechst was added to the culture medium two hours before examination. Cells were examined under FITC filter on a Leica microscope equipped with photo camera.

Confocal Microscopy Imaging

Cells growing on glass coverslips were transiently transfected with either Xcml-GFP expression construct or XcmlF2-GFP using FuGene 6 transfection kit (Boehringer Mannheim) 36 h prior to fluorescence analysis. Golgi apparatus was stained by treatment of cells with 0.5 mM BODIPY TR ceramide (Molecular Probes) for 1 h. After loading, the cell were washed twice with and kept in Dulbecco/PBS solution containing 20 mM HEPES, pH 7.4 at room temperature for 20 min prior to the experiments. The fluorescence in living cells was analyzed using a Bio-Rad MRC-1024 confocal microscope equipped with an argon-krypton laser.

Expression of the Members of Camello Family

The effect on cell adhesion of overexpression of Xcml and a human member of the camello family (Hcml1) was studied using blastomere aggregation assay. For the aggregation assay, 2 ng of Xcml or XcmlA31Fr (mutant with the frameshift after Ala31, which served as a negative control) mRNA were injected into the animal pole of blastomeres at the 4-cell stage. Animal caps were isolated at stage 8, and the blastomeres were dissociated in calcium/magnesium-free MMR medium (100 mM NaCl; 2 mM KCl; 5 mM Hepes, pH 7.6; 0.1 mM EDTA) by passing several times through the plastic tip. Calcium was added to the medium, to a concentration of 2 mM, and blastomeres were allowed to aggregate on a horizontal rotary shaker at 60 rpm in 35-mm dishes coated with 1% agarose (10 caps per dish). After incubation for 30 to 40 min, cells were fixed by addition of formaldehyde to 4%.

The aggregates were divided into five size classes and quantified. The size classes consisted of: a) single cells; b) 2–4 cells; c) 5–7 cells; d) 8–10 cells; and e) more then 10 cells per aggregate. Differences in the total number of cells in aggregates of each size class after injection of Xcml and XcmlA31Fr were evaluated in eight experiments. The Wilcoxon test was used for statistical comparisons. P values less than 0.05 were accepted as indicating statistically-significant differences between the two samples. For analysis of Hcml1 influence on cell adhesion, effects of injection of 2 ng of Hcml1 RNA or of XcmlA31Fr RNA were compared.

2. Results and Discussion

To identify genes potentially involved in regulation of gastrulation, Gene Expression Fingerprinting technique (Ivanova and Belyavsky, *Nucl. Acid Res.* 23: 2954–2958 (1995)) was used to search for genes expressed differentially in subregions of Xenopus gastrula embryos. One of the identified sequences (N4) was found to be expressed specifically in the dorsal and ventral marginal zones (Ivanova, et al., *Dokl. Acad. Nauk* 359:116–119 (1998)) at the beginning of gastrulation, and its detailed study is described herein. A cDNA clone isolated from gastrula library encodes the predicted protein 219 amino acids long (FIG. 1B) containing an internal 40-amino acid long hydrophobic region with a short hydrophilic stretch in the middle suggesting that the protein can be membrane associated. At the same time, no N-terminal hydrophobic leader peptide sequence typical for transmembrane proteins could be found. Due to the characteristic hydrophobicity profile of the encoded protein the gene was named camello (Spanish for camel).

Searches in the EST database revealed four murine (Mcml1–4), two rat (Rcml1,2) and one human (Hcml1) non-identical cDNA sequences encoding putative proteins with significant homology to Xenopus camello (Xcml) and to each other. A second human putative member of this family was identified in the Huntington gene region whereas TSC501 gene (Ozaki, et al., *J. Hum. Genet.* 43, 255–258 (1998)) is virtually identical to the human Hcml1 gene. Deduced amino acid sequences of the mammalian camello family are shown on FIG. 14. At amino acid level, Xcml is 37% identical to human/mouse, whereas the human-mouse identity is 60% with conservative replacements. Mammalian homologues also demonstrate a striking similarity to Xcml at the structural level, including the presence of hydrophobic domain, its length, organization and the distance from the N-terminus. Moreover, C-terminal regions of Xenopus and mammalian members of camello family demonstrate statistically significant homology to the different members of the large family of N-acetyltransferases present in bacteria, fungi and animals (Lee, et al., *J. Biol. Chem.* 263:14948–14955 (1988); Hintermann, et al., *FEBS Lett.* 375:148–150 (1995); Ebisawa et al., *Eur. J. Biochem.* 228:129–137 (1995)). The maximum degree of identity of camello family members to N-acetyltransferases is 25–30%, fairly similar to the homology between different N-acetyltransferase groups (Coon, et al., *Science* 270:1681–1683 (1995)). Two structural domains responsible for Ac CoA binding (domain A) and acetyl group transfer (domain B) were identified in N-acetyltransferases (Schulz, *Curr. Opin. Struct. Biol.* 2:61 (1992)). All camello family members match well the consensus motifs in both A and B N-acetyltransferase domains. It should be noted that no N-acetyltransferases with extended hydrophobic regions have been reported, and the only member of this family with a demonstrated role in embryo development is the Hookless participating in plant morphogenesis. On the basis of protein sequence analysis it is suggested that the camello family is a novel and highly distinct subgroup of N-acetyltransferases.

Temporal pattern of Xcml gene expression was studied by the Northern blot analysis (FIG. 15A). Xcml gene encodes a c.a. 1.4 kb transcript that appears after MBT, reaches its expression maximum at the stage 10 and continues to be expressed at similar levels until at least stage 27.

Figure 15B:
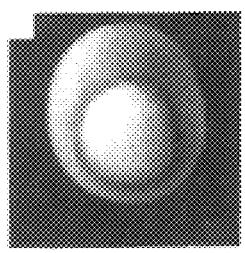
Figure 15C:
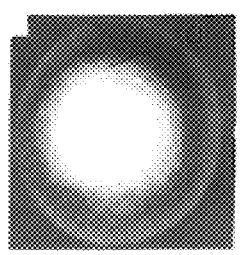
Figure 15D:
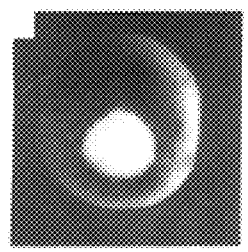
Figure 15E:
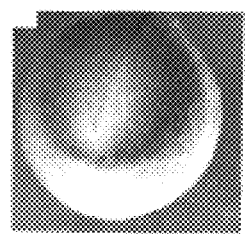
Figure 15F:
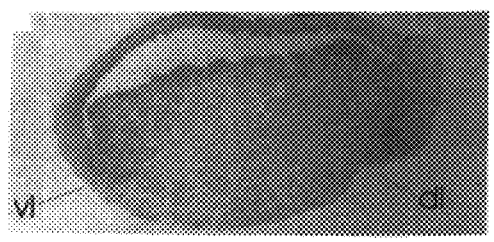
Figure 15G:
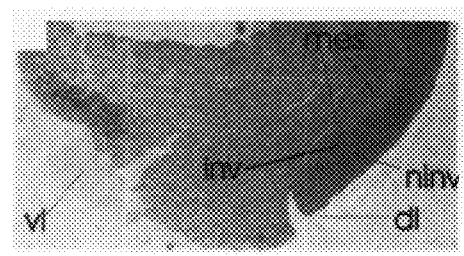
Figure 15H:
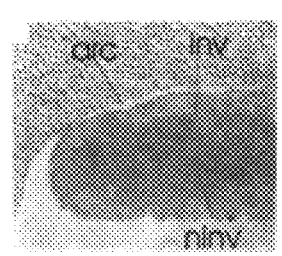
Figure 16E:
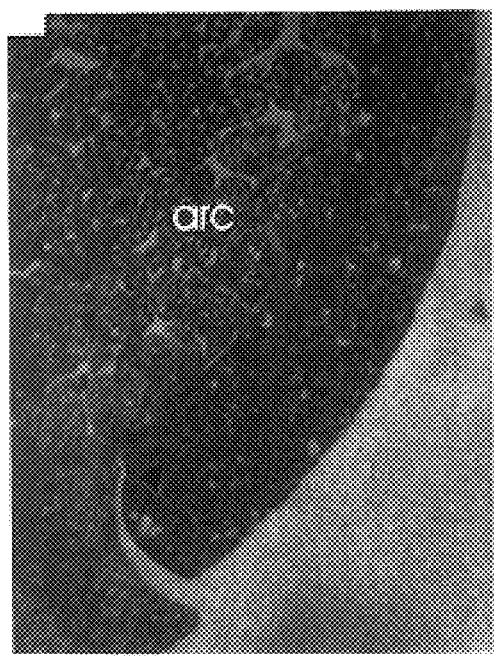
FIG. 16 depicts Xcml overexpression blocking gastrulation movements of cells. Injection of Xcml mRNA in 2 dorsal vegetal blastomeres retards gastrulation (a); blastopore of injected embryos is longer in dorso-ventral direction as a result of suppression of latero-medial movements and intercalation of cells on dorsal side of embryo. At neurula stage injected embryos have short axis and unclosed blastopore (b). Sagittal sections (c–f) of embryos from a show decrease of adhesive properties of cells in injected half of embryo (d, f). Involuted cells form multilayer epithelial structure at the dorsal side (e), but lost this capacity after Xcml overexpression (f). At the neurula stage, injected embryo (g, h) has defect structure of neural plate (np), sometes (som), and disrupted gastrocoel (gc, h).
Figure 16F:
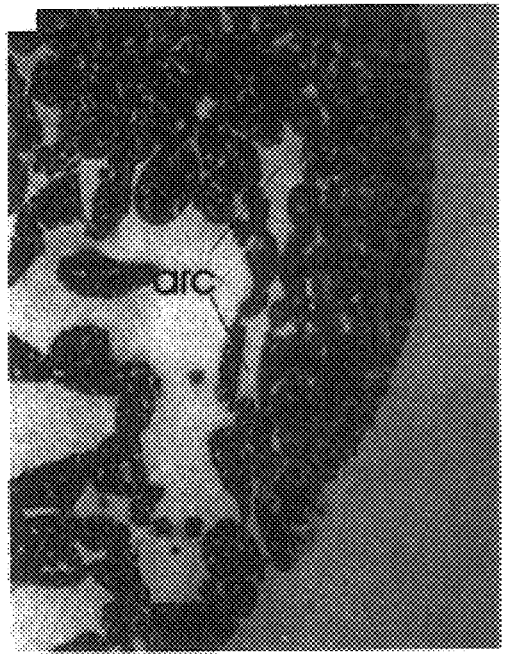
Figure 16G:
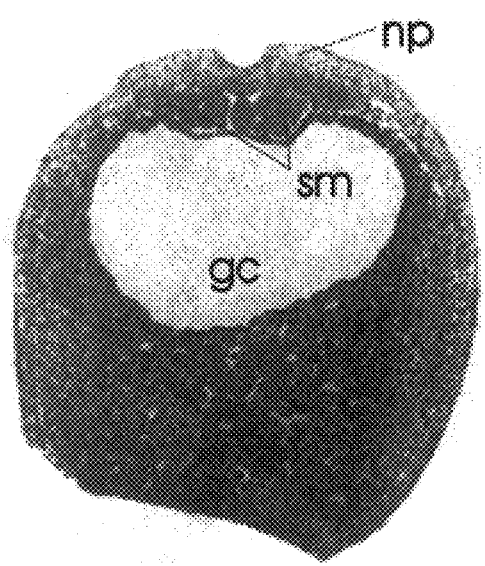
Figure 16H:
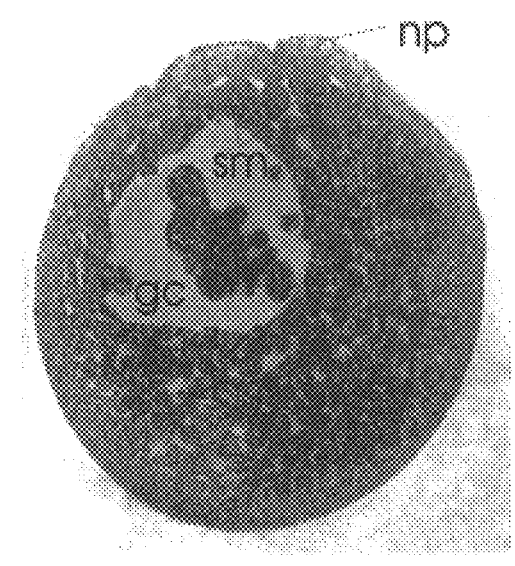

Whole-mount in situ hybridization using a digoxygenine-labeled Xcml RNA antisense probe (FIG. 15B) revealed that the first weak signal appears in the marginal zone of embryo at the beginning of gastrulation (stage 10), in the region of presumptive chordamesoderm. Xcml is expressed in deep cells of this zone. Bottle cells—the leading cells of dorsal lip—are not stained. Larger magnification reveals mosaic staining of marginal zone with many cells not stained. At stages 11,5 and 12 Xcml message is expressed in the same ring of deep cells around the closed blastopore. During gastrulation marginal zone cells initially expressing Xcml involute, perform convergent-intercalation movements and form axial structures (chorda and somites) at the dorsal side of embryo. However, hybridization data demonstrate that whereas Xcml is expressed in the surface cells of periblastopore region, these cells cease to express gene after they involute inside the embryo. This expression pattern is substantially different from that of other genes expressed in presumptive mesoderm, most of which continue to be expressed after involution. At late neurula and tailbud stages, Xcml transcripts are found in the deep mass of cells lying ventrally and laterally to the chordoneural hinge.

To investigate the role that Xcml might play during early development, in vitro synthesized Xcml mRNA was injected into equatorial region of dorsal or ventral blastomeres of 8-cell stage embryos. With dorsal injection, development proceeded normally until the late blastula, but during gastrulation the involution of mesoderm in the majority (up to 70%) of injected embryos was greatly inhibited. Blastopore closure did not occur completely (FIG. 16, Table 1 below) and until neurula stages most of the embryos keep open blastopores of different sizes; in some abnormal embryos blastopore closure did not occur at all. In these cases, mesodermal cells during epiboly spread along the big blastopore resulting in two bands of axial tissue on each side of the blastopore. The multilayer accumulation of mesodermal cells in ventro-lateral region of the blastopore was detected on the sagittal sections of dorsally injected embryos. The suppression of radial intercalation movements led to the phenotype with shortened antero-posterior axis with severely truncated head structures and neural plate. Little if any developmental defects were observed in embryos injected with the same amounts of actin mRNA. Introduction of the frame-shift after Ala31 or the stop-codon after Ala32 (constructs XcmlA31F and XcmlA32S, respectively) resulted in complete elimination of developmental abnormalities demonstrating the specificity of effects produced by camello RNA.

When ventral blastomeres were injected, embryos appeared normal until the late gastrula stages. Embryos successfully formed ventral lip, but mesodermal cells accumulated in the lateral region which became apparent in asymmetrically injected embryos with curved posterior parts of axial complexes (FIG. 16).

To study in more detail the developmental defects produced by Xcml overexpression, whole-mount in situ hybridization of injected embryos with mesodermal and neural tissue markers such as Xbra, Xnot, b-tubulin, eng, Pax6, gsc, chr, nog, BMP4 was performed. Observed patterns were fully compatible with morphological changes caused by defects in gastrulation (FIG. 16). Therefore, overexpression of Xcml, apart of mechanistic effects, seems to induce little if any changes in gene expression or in the determination of the cell layers.

Dorsal overexpression of Xcml mutant protein with deletion of N-acetyltransferase domain but intact N-terminal two thirds had essentially no effect on gastrulation indicating that the deleted domain is necessary for the function of the protein. At the same time, overexpression of the Xcml mutant (XcmlDF42L80) devoid of the entire hydrophobic domain showed moderate, two- to three-fold, reduction in the percentage of gastrulation defects compared to the intact protein, suggesting that the hydrophobic domain, although essential, is not indispensable for camello function.

TABLE 1

Xcml overexpression inhibits gastrulation movements and induction of the ectopic axis

| | n | Abnormalities of development (%) | Complete secondary axis (%) | Reduced secondary axis (%) |
|---|---|---|---|---|
| Xcml | 125 | 77 | | |
| | 160 | 58 | | |
| Actin | 159 | 2 | | |
| XcmlA31F | 72 | 0 | | |
| XcmlJ | 79 | 0 | | |
| XcmlDF42L80 | 89 | 29 | | |
| Mcml 1 | 39 | 50 | | |
| Hcml1 | 74 | 50 | | |
| Goosecoid (60 pg) | 25 | | 50 | 50 |
| Goosecoid (60 pg) + Xcml (1 ng) | 37 | | 25 | 75 |

For experiments where inhibition of gastrulation movements were examined, 8-cell stage embryos were injected in two dorsal vegetal blastomeres with 2 ng per embryo of the indicated RNAs. In assay of ectopic axis induction, the same stage embryos were injected in two ventral vegetal blastomeres, and secondary axes were scored at the tailbud stage. Duplicated axes were scored as complete when showing cement gland and eyes, and as reduced when lacking both features.

Figure 17A:
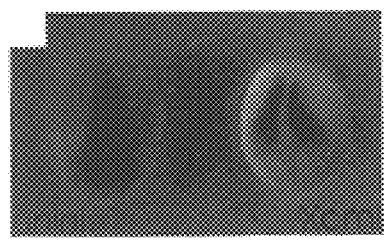
FIG. 17 depicts the effects of Xcml injections on expression pattern of early markers and goosecoid-induced formation of second axis. Expression patterns of actin (a), Xbra (b), Xnot (d, e) marks abnormal position of presumptive materials after Xcml injection. Xcml decreases expression of Pax-6(c) in posterior part of neural tube and in axial complexes in lateral lips of unclosed blastopore. (f) Injection of gsc in two ventral vegetal blastomeres leads to the formation of full second axis with head structures (eyes, cement glands); (g) co-injection of gsc with Xcml leads to the reduction of head structures.
Figure 17B:
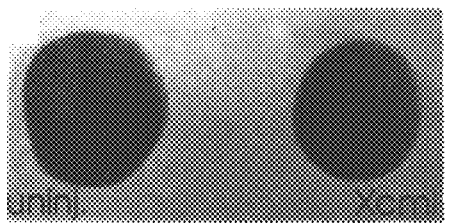
Figure 17C:
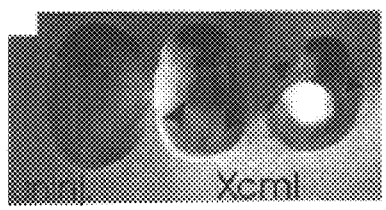
Figure 17F:
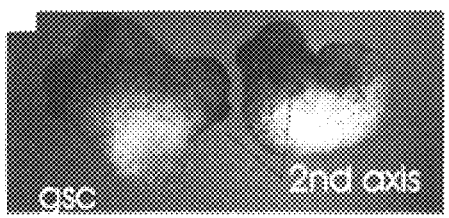
Figure 17D:
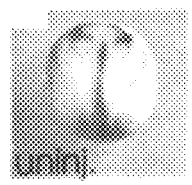
Figure 17E:
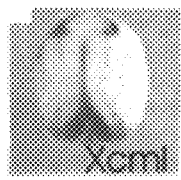
Figure 17G:
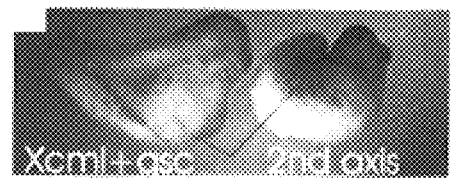

Sections were prepared to study overexpression Xcml on cell morphology. There are large spaces between cells and cavities in injected dorsal part of embryos as compared with ventral part (FIG. 17b) and intact embryos (FIG. 17c). Cells change from polygonal shape to elongate. Involuted cells of intact embryos form multilayer epithelial structure at dorsal side (future chorda and somites) (FIG. 17d), epithelial sheets form archenteron. Overexpression Xcml disorders epithelial structures (FIG. 17e). Observations allow to suppose about decreasing adhesion ability by descendants of injected Xcml blastomeres. Changes of morphogenetic behavior of cells through gastrulation led to morphology defects at neurula stage: abnormal structure of neural plate, somites, asymmetric position and disruption of integrity of gastrocoel.

Ectopic expression of goosecoid on the ventral side of embryo induces a massive cell movement at the early gastrula stage toward the anterior of the embryo and formation of second axis (Niehrs, et al., *Cell* 72:491–503 (1993)). Xcml evidently antagonizes this action of goosecoid since co-injection of Xcml and goosecoid mRNAs in two ventral blastomeres led to the decrease of formation of complete secondary axes from 60% in embryos injected with gsc alone to 27% in co-injected embryos. This result presents an additional evidence for an inhibitory effect of Xcml overexpression on gastrulation movements.

The possible function of mammalian members of camello family was studied by injection of RNA of Mcml4 and Hcml1 genes into Xenopus dorsal blastomeres. In both cases the nature and magnitude of developmental effects were quite similar to those observed with control injections of Xcml RNA (Table 1, above) suggesting the similarity of mechanisms of action and possibly in vivo functions of mammalian and Xenopus camello proteins.

To determine the intracellular localization of Xcml protein, the inventors performed the confocal microscopy of COS-7 cells transfected with the Xcml-GFP fusion expression construct. The majority of fluorescent signal was found in compact perinuclear lamellar or vesicular structure characteristic for the Golgi complex (FIG. 18). A weaker and more variable staining of a fine reticular structure, evidently endoplasmatic reticulum, was also detected. When Xcml-GFP-transfected cells were stained with a Golgi-specific dye BODIPY TR ceramide, a significant overlap between green GFP signal and red ceramide signal was observed thereby confirming the preferential localization of the fused protein in the Golgi apparatus. The hydrophobic domain of Xcml is likely to serve as a transmembrane anchor, presumably in a shape of two membrane-spanning a-helices. Deletion of the hydrophobic domain resulted in a marked delocalization of the fused protein, with significant proportion of the signal detected in the nucleus and cytoplasm (FIG. 18). However, a certain degree of co-localization of the GFP and ceramide signals, although reduced, was still observed. Therefore, it is likely that the hydrophobic domain is essential for the Golgi localization of the Xcml protein; however, it is possibly not the sole targeting signal. As evidenced by injection studies, membrane anchoring seems to be important but not indispensable for Xcml function. The residual activity of mutant protein devoid of membrane anchor might be explained by the part of protein which is still localized to the lumen of secretory pathway organelles, however, more experiments are needed to clarify the issue.

Localization of the Xcml protein to organelles of the secretory pathway suggested the possibility that Xcml might be secreted. To test this, synthetic mRNAs of Xcml with myc epitope tags at the C- or N-terminus were microinjected into Xenopus oocytes followed by Western blotting analysis of the culture medium and vesicular and cytoplasmic fractions of oocytes. Myc tag-containing bands of predicted size were detected only in vesicular fraction (FIG. 18e). When a similar experiment was performed with myc tagged form of secreted protein, immunoreactivity in the culture medium could be easily detected. Hence, Xcml is unlikely to be a secreted protein.

Figure 19:
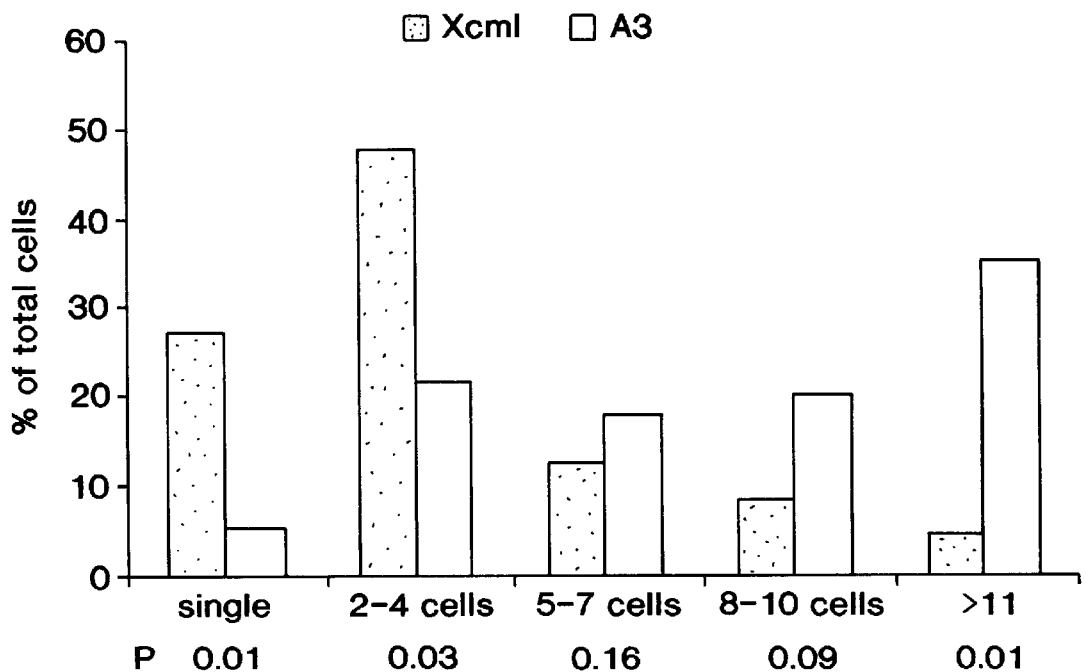
FIG. 19 depicts an example of the blastomere aggregation assay for analysis of Xcml function. The number of cells in each aggregate class is indicated on the horizontal axis, and the percentage of cells in each aggregate class is indicated on the vertical axis. The results for injection of identical amounts of Xcml and XcmlA31Fr (A3) RNA are compared. P values on the horizontal axis indicate the probability that the difference between Xcml and the negative control is non-significant. The data demonstrate that Xcml injection substantially reduces blastomere aggregation, since the percentage of single cells after Xcml injection increased 4-fold, while the percentage of large (more than 10 cells) aggregates decreased more than 6-fold in this example.
Figure 20:
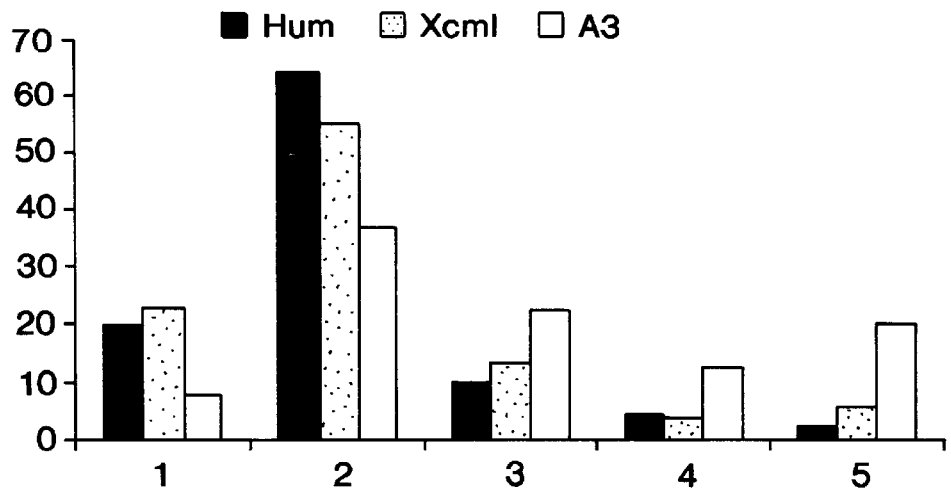
FIG. 20 depicts the blastomere aggregation assay for Hcml1 RNA. Graph details are the same as in FIG. 19. On the horizontal axis, the following aggregate size classes are shown: 1: single cells; 2: 2–4 cells; 3: 5–7 cells; 4: 8–10 cells; and 5: more than 10 cells. Compared are the effects on Ca-induced blastomere re-aggregation of injection of identical amounts of Xcml, Hcml1 (Hum), or XcmlA31Fr (A3) RNA. The data indicate that Hcml1 (like Xcml) substantially reduces adhesion of blastomeres. After Hcml1 injection, the number of single cells is increased approximately 2.5-fold, whereas the number of cells in large (more than 10 cells) aggregates is reduced more than 5-fold compared to the negative control (A3).

The results of blastomere aggregation assays (FIGS. 19 and 20) indicated clearly that Xcml and a human member of the camello family, Hcml1, have a substantial anti-adhesive effect, which confirms earlier data obtained by microscopic observation of Xcml-overexpressing embryos. The blastomere aggregation assay was calcium-based and, therefore, primarily driven by the cadherin adhesion. It has been convincingly demonstrated (Brieher, et al., *J. Cell. Biol.* 126:519–27 (1994); Zhong, et al., *J. Cell. Biol.,* 144:351–59 (1999)) that cadherin C is a major determinant of adhesion in this assay. Therefore, the cadherins, including cadherin C, are the likely targets of Xcml action. Of course, participation of other cell surface or extracellular proteins in Xcml-related anti-adhesive effects remains a definite possibility.

Adhesion is one of the most important mechanisms participating in cancer metastasis, and adhesion proteins (particularly cadherins) have been shown to be important for metastatic processes. Therefore, the camello family proteins, with their anti-adhesive effects and potential targeting of cadherin-mediated adhesion, are good candidates for the development of anti-metastatic drugs.

It is known that gastrulation movements are maintained by a fine balance of spatially and temporally regulated adhesion. The phenotypes similar to the one produced by overexpression of Xcml can be generated by perturbation of cell adhesion by interference with function of different cadherins or extracellular matrix proteins. Xcml is expressed throughout gastrulation in a critically important region where convergent extension and invagination occur, and its overexpression induces defects similar to those produced by strong reduction of cell adhesion. It is tempting therefore to assume that the normal Xcml function might involve moderate reduction in adhesion of cells located in or moving through the periblastopore region, resulting in change of their migratory properties. This assumption is supported by animal cap elongation experiments which suggest that a controlled reduction of cell adhesion is necessary for gastrulation (Brieher, et al., *J. Cell. Biol.* 126:519–27 (1994)).

Xcml is preferentially localized in Golgi apparatus, which is the major site of synthesis of extracellular matrix proteins as well as terminal processing of cell surface glycoproteins involved in cell adhesion. It is likely that this connection is not coincidental, and that the mechanism of Xcml action may involve participation in the processing of cell surface or extracellular matrix proteins passing through secretory pathway. The strong similarity of Xcml and other members of this family to the two consensus motifs of N-acetyltransferases makes acetylation a natural candidate for this modification. So far, the most prominent acetylation reaction known to occur in Golgi complex is an O-acetylation of sialylic acids in glycoproteins and glycolipids by as yet unidentified enzyme(s). O-acetylation of glycoproteins was shown to change their ashesion to selectins. Whether Xcml may encode sialyc acid O-acetyltransferase remains to be seen, however, the difference between the consensus motifs for N- and O-acetyltransferases does not support this hypothesis.

Camello family can be added to a growing list of proteins such as fringed or Kuzbanian which are localized in Golgi complex and are involved in the regulation embryogenesis. Further, the anti-adhesive effects of camello family proteins may be implicated in metastasis and tumor aggression, making the proteins an attractive target for anti-metastatic and chemotherapeutic agents.

All publications mentioned hereinabove are hereby incorporated by reference in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. An isolated nucleic acid encoding a camello protein, wherein the camello protein consists of an amino acid sequence selected from the group consisting of SEQ ID NO:4, SEQ ID NO:6, and SEQ ID NO:8.

2. The nucleic acid of claim 1, wherein the amino acid sequence is SEQ ID NO:4.

3. The nucleic acid of claim 1, having the nucleotide sequence selected from the group consisting of SEQ ID NO:3, SEQ ID NO:5, and SEQ ID NO:7.

4. The nucleic acid of claim 1, wherein the nucleotide sequence is SEQ ID NO:3.

5. A vector comprising the nucleic acid sequence of claim 1.

6. A vector comprising the nucleic acid sequence of claim 2.

7. A vector comprising the nucleic acid sequence of claim 3.

8. A vector comprising the nucleic acid sequence of claim 4.

9. A host cell comprising the vector of claim 5.

10. A host cell comprising the vector of claim 6.

11. A host cell comprising the vector of claim 7.

12. A host cell comprising the vector of claim 8.

13. The host cell of claim 9, wherein the host cell is a prokaryotic cell.

14. The host cell of claim 9, wherein the host cell is a eukaryotic cell.

15. A method for producing a recombinant camello protein, comprising growing the host cell of claim 13 in a culture and isolating the recombinant camello protein from the culture.

16. A method for producing a recombinant camello protein, comprising growing the host cell of claim 14 in a culture and isolating the recombinant camello protein from the culture.

17. A method for producing a recombinant camello protein, comprising growing the host cell of claim 11 in a culture and isolating the recombinant camello protein from the culture.

18. A method for producing a recombinant camello protein, comprising growing the host cell of claim 12 in a culture and isolating the recombinant camello protein from the culture.

19. The nucleic acid of claim 1, wherein the amino acid sequence is SEQ ID NO:6.

20. The nucleic acid of claim 1, wherein the amino acid sequence is SEQ ID NO:8.

* * * * *

SEQUENCE LISTING

<160> NUMBER OF SEQ ID NOS: 26

<210> SEQ ID NO 1
<211> LENGTH: 1225
<212> TYPE: DNA
<213> ORGANISM: Xenopus laevis

<400> SEQUENCE: 1

| | | | | | |
|---|---|---|---|---|---|
| gcacgagcaa | gctgctttct | cgttatttct | tctgttcccc | cggaacagga | ctcatataag | 60 |
| atccttctgt | agttataggt | ggaggccttt | gctcagtcgg | agtatcatgg | ccaacgtctc | 120 |
| cataagaaaa | tacaaaaaca | gtgactatga | aacggtcaac | ttcttgtttg | ttgaaggaac | 180 |
| aaaagagcat | ctcccagcag | cctgttggaa | cacactgaag | aagcctcggt | tttatttcat | 240 |
| cattattgtg | gcatgtgcca | gcatcttcat | gtgcaccagt | tcctatgttc | tgtcccttac | 300 |
| aagccttgtt | gccctgttgg | ctgttggctg | gtatggcttg | tacttggaat | tccatgggta | 360 |
| tgcaagtcgg | tgccagcgtg | aggatatgct | tgatattgag | aattcctaca | tgatgagtga | 420 |
| caatacttgt | ttctgggtgg | cagagataga | caggaaggtt | gtgggcatag | tgggtgccaa | 480 |
| accattaaaa | gaagcagatg | atgagctgtt | tctgttacat | ctctctgttg | ccagggactg | 540 |
| tcgccagcag | cggattggca | caaagctgtg | ccagacagtc | attgattttg | ccaggcagcg | 600 |
| tggtttcaaa | gctgtgtgtc | tggaaacagc | aaacatacaa | gacgcagcaa | taaagttgta | 660 |
| tgaagccgtt | ggctttaaga | atcccttgt | tgcaatcccc | ccattccttc | ttaaccaata | 720 |
| cacatctttc | acagttattt | attacagata | tgatatcaaa | tcataggaaa | tccagtgctt | 780 |
| aataatccat | aggacacaat | cttctgccac | cttccatcag | caccggccta | cagccacatc | 840 |
| aactggtttc | atgagcagaa | tcagaaccta | agatccaaga | tgagtctgaa | accctacaga | 900 |
| ctggagaaga | ggaaccagtt | cagatggtta | ttactaaatt | cattttggaa | agccaccatg | 960 |
| gaagggaag | ctccagaagc | ctcctgagat | gtttcacttt | caatgtcaaa | agaaaaataa | 1020 |
| acagtagaca | aactaatatc | aacaagtgtg | ggatcgactc | tgtccacatg | atgtggagta | 1080 |
| agaaatttaa | ccaatcttaa | atcaaagctg | ggtatcagtc | aattttttctt | gattttactc | 1140 |
| ttagagtttt | ttaaacacag | gacatgtcat | atgcatttct | tctgatattc | cttcccatgt | 1200 |
| cttgctatta | aacagcatat | ttgtt | | | | 1225 |

<210> SEQ ID NO 2
<211> LENGTH: 219
<212> TYPE: PRT
<213> ORGANISM: Xenopus laevis

<400> SEQUENCE: 2

Met Ala Asn Val Ser Ile Arg Lys Tyr Lys Asn Ser Asp Tyr Glu Thr
1               5                  10                  15

Val Asn Phe Leu Phe Val Glu Gly Thr Lys Glu His Leu Pro Ala Ala
            20                  25                  30

Cys Trp Asn Thr Leu Lys Lys Pro Arg Phe Tyr Phe Ile Ile Ile Val
        35                  40                  45

Ala Cys Ala Ser Ile Phe Met Cys Thr Ser Ser Tyr Val Leu Ser Leu
    50                  55                  60

Thr Ser Leu Val Ala Leu Leu Ala Val Gly Trp Tyr Gly Leu Tyr Leu
65                  70                  75                  80

Glu Phe His Gly Tyr Ala Ser Arg Cys Gln Arg Glu Asp Met Leu Asp
                85                  90                  95

```
Ile Glu Asn Ser Tyr Met Met Ser Asp Asn Thr Cys Phe Trp Val Ala
            100                 105                 110
Glu Ile Asp Arg Lys Val Val Gly Ile Val Gly Ala Lys Pro Leu Lys
        115                 120                 125
Glu Ala Asp Asp Glu Leu Phe Leu Leu His Leu Ser Val Ala Arg Asp
    130                 135                 140
Cys Arg Gln Gln Arg Ile Gly Thr Lys Leu Cys Gln Thr Val Ile Asp
145                 150                 155                 160
Phe Ala Arg Gln Arg Gly Phe Lys Ala Val Cys Leu Glu Thr Ala Asn
                165                 170                 175
Ile Gln Asp Ala Ala Ile Lys Leu Tyr Glu Ala Val Gly Phe Lys Lys
            180                 185                 190
Ser Leu Val Ala Ile Pro Pro Phe Leu Leu Asn Gln Tyr Thr Ser Phe
        195                 200                 205
Thr Val Ile Tyr Tyr Arg Tyr Asp Ile Lys Ser
    210                 215

<210> SEQ ID NO 3
<211> LENGTH: 1009
<212> TYPE: DNA
<213> ORGANISM: Homo sapiens

<400> SEQUENCE: 3
ccttgggmca gmmttcggca cgagcggcac gagaagcccc agacggtatc tccgagatgc      60
cagtgagcgg ctgagagctg aagcccctg gacactcaag gctcttgtgg tgacagtctg     120
acgtaaaggc gtgcagggag cctagctct gtctcctgga cttagagatt tcagacacag     180
aagtctgtcc atggctcctt gtcacatccg caaataccag gagagcgacc gccagtgggt     240
tgtgggcttg ctctccggg ggatggccga gcatgcccca gccaccttcc ggcaattgct     300
gaagctgcct cgaaccctca tactcttact tggggggccc ctcgccctac tcctggtctc     360
tggatcctgg cttctagccc tcgtgttcag catcagcctc ttccctgccc tgtggttcct     420
tgccaaaaaa ccctggacgg agtatgtgga catgacattg tgcacagaca tgtctgacat     480
taccaaatcc tacctgagtg agcgtggctc ctgcttctgg gtggctgagt ctgaagagaa     540
ggtggtgggc atggtaggag ctctgcctgt tgatgatccc accttgaggg agaagcggtt     600
gcagctgttt catctctctg tggacagtga gcaccgtcgt cagggatag caaaagccct      660
ggtcaggact gtcctccagt ttgcccggga ccagggctac agtgaagtta tcctggacac     720
cggcaccatc cagctctctg ctatggccct ctaccagagc atgggcttca agaagacggg     780
ccagtccttc ttctgtgtgt gggccaggct agtggctctt catacagttc atttcatcta     840
ccacctccct tcttctaagg tagggagtct gtgatctctt tctgtgtgta ttggtcagaa     900
tagaatccat tcagctgtag cagcaagcaa tccccaacct ttcactgcaa tgacctttca     960
atgcaataaa agcttattgt ccattcaaaa aaaaaaaaa aaaaagatc                 1009

<210> SEQ ID NO 4
<211> LENGTH: 227
<212> TYPE: PRT
<213> ORGANISM: Homo sapiens

<400> SEQUENCE: 4

Met Ala Pro Cys His Ile Arg Lys Tyr Gln Glu Ser Asp Arg Gln Trp
1               5                   10                  15
Val Val Gly Leu Leu Ser Arg Gly Met Ala Glu His Ala Pro Ala Thr
```

```
                  20                  25                  30
Phe Arg Gln Leu Leu Lys Leu Pro Arg Thr Leu Ile Leu Leu Leu Gly
             35                  40                  45

Gly Pro Leu Ala Leu Leu Val Ser Gly Ser Trp Leu Leu Ala Leu
 50                  55                  60

Val Phe Ser Ile Ser Leu Phe Pro Ala Leu Trp Phe Leu Ala Lys Lys
 65                  70                  75                  80

Pro Trp Thr Glu Tyr Val Asp Met Thr Leu Cys Thr Asp Met Ser Asp
                 85                  90                  95

Ile Thr Lys Ser Tyr Leu Ser Glu Arg Gly Ser Cys Phe Trp Val Ala
                100                 105                 110

Glu Ser Glu Lys Val Val Gly Met Val Gly Ala Leu Pro Val Asp
            115                 120                 125

Asp Pro Thr Leu Arg Glu Lys Arg Leu Gln Leu Phe His Leu Ser Val
    130                 135                 140

Asp Ser Glu His Arg Arg Gln Gly Ile Ala Lys Ala Leu Val Arg Thr
145                 150                 155                 160

Val Leu Gln Phe Ala Arg Asp Gln Gly Tyr Ser Glu Val Ile Leu Asp
                165                 170                 175

Thr Gly Thr Ile Gln Leu Ser Ala Met Ala Leu Tyr Gln Ser Met Gly
            180                 185                 190

Phe Lys Lys Thr Gly Gln Ser Phe Phe Cys Val Trp Ala Arg Leu Val
        195                 200                 205

Ala Leu His Thr Val His Phe Ile Tyr His Leu Pro Ser Ser Lys Val
        210                 215                 220

Gly Ser Leu
225

<210> SEQ ID NO 5
<211> LENGTH: 830
<212> TYPE: DNA
<213> ORGANISM: Homo sapiens

<400> SEQUENCE: 5
ctggactcag tgacttcaga cacagaagtc tgtccatggc tccttatcac atccgcaaat    60
accaggagag cgaccgcaag tcggtcgtgg gcttgctctc cggggggatg gccgaacacg   120
ccccagccac cttccggcga ttactgaagc tgcctcgaac cctcatactc ttacttgggg   180
gggcccttgc cctactcctg gtctctggct cctggattct ggccctcgtg ttcagcctca   240
gcctccttcc tgccctgtgg ttccttgcca aaaaccctg gacgcggtat gtagacatag   300
cattgcgcac agacatgtct gacatcacca atcctacct gagtgagtgt ggctcctgct   360
tctgggtggc tgaatctgaa gagaaggtgg tgggcacagt aggagctctg cccgttgatg   420
atcccacctt gagggagaag cggttgcagc tgtttcatct ctctgtggac aatgagcacc   480
gtggtcaggg gatagcaaaa gccctggtca ggactgtcct ccagtttgcc cggaccagg    540 gctacagtga agttgtcctg gacaccagca acatccagct ctctgccatg ggcctctacc   600
agagcttggg cttcaagaag acgggccagt ccttcttcca cgtgtgggcc aggctggtgg   660
atcttcatac agttcatttc atctatcacc tcccttctgc tcaggcaggg cgtctatgat   720
ttctttcctt ctgtattggt cagaatagaa tccattcggc tgtagcagca agcaatcccc   780
aacctctgac tgcaatgacc tttctgtgca ataaaagctt attgtccatt               830

<210> SEQ ID NO 6
```

```
<211> LENGTH: 227
<212> TYPE: PRT
<213> ORGANISM: Homo sapiens

<400> SEQUENCE: 6

Met Ala Pro Tyr His Ile Arg Lys Tyr Gln Glu Ser Asp Arg Lys Ser
1               5                   10                  15

Val Val Gly Leu Leu Ser Gly Gly Met Ala Glu His Ala Pro Ala Thr
            20                  25                  30

Phe Arg Arg Leu Leu Lys Leu Pro Arg Thr Leu Ile Leu Leu Leu Gly
        35                  40                  45

Gly Ala Leu Ala Leu Leu Val Ser Gly Ser Trp Ile Leu Ala Leu
    50                  55                  60

Val Phe Ser Leu Ser Leu Leu Pro Ala Leu Trp Phe Leu Ala Lys Lys
65                  70                  75                  80

Pro Trp Thr Arg Tyr Val Asp Ile Ala Leu Arg Thr Asp Met Ser Asp
                85                  90                  95

Ile Thr Lys Ser Tyr Leu Ser Glu Cys Gly Ser Cys Phe Trp Val Ala
            100                 105                 110

Glu Ser Glu Glu Lys Val Val Gly Thr Val Gly Ala Leu Pro Val Asp
        115                 120                 125

Asp Pro Thr Leu Arg Glu Lys Arg Leu Gln Leu Phe His Leu Ser Val
    130                 135                 140

Asp Asn Glu His Arg Gly Gln Gly Ile Ala Lys Ala Leu Val Arg Thr
145                 150                 155                 160

Val Leu Gln Phe Ala Arg Asp Gln Gly Tyr Ser Glu Val Leu Asp
                165                 170                 175

Thr Ser Asn Ile Gln Leu Ser Ala Met Gly Leu Tyr Gln Ser Leu Gly
            180                 185                 190

Phe Lys Lys Thr Gly Gln Ser Phe Phe His Val Trp Ala Arg Leu Val
        195                 200                 205

Asp Leu His Thr Val His Phe Ile Tyr His Leu Pro Ser Ala Gln Ala
    210                 215                 220

Gly Arg Leu
225

<210> SEQ ID NO 7
<211> LENGTH: 432
<212> TYPE: DNA
<213> ORGANISM: Homo sapiens

<400> SEQUENCE: 7
gcgctgtgct tcgccgtgag ccgctcgctg ctgctgacgt gcctggtgcc ggccgcgctg     60
ctgggcctgc gctactacta cagccgcaag gtgatccgcg cctacctgga gtgcgcgctg    120
cacacggaca tggcggacat cgagcagtac tacatgaagc cgcccggctc ctgcttctgg    180
gtggccgtgc tggatggcaa cgtggtgggc attgtggctg cacgggccca cgaggaggac    240
aacacggtgg agctgctgcg gatgtctgtg gactcacgtt tccgaggcaa gggcatcgcc    300
aaggcgctgg ccggaaggt gctggagttc gccgtggtgc acaactactc cgcggtggtg    360
ctgggcacga cggccgtcaa ggtggccgcc cacaagctct acgagtcgct gggcttcaga    420
cacatgggcg cc                                                        432

<210> SEQ ID NO 8
<211> LENGTH: 144
<212> TYPE: PRT
```

<213> ORGANISM: Homo sapiens

<400> SEQUENCE: 8

| Ala | Leu | Cys | Phe | Ala | Val | Ser | Arg | Ser | Leu | Leu | Leu | Thr | Cys | Leu | Val |
|---|---|---|---|---|---|---|---|---|---|---|---|---|---|---|---|
| 1 | | | | 5 | | | | | 10 | | | | | 15 | |

Pro Ala Ala Leu Leu Gly Leu Arg Tyr Tyr Tyr Ser Arg Lys Val Ile
     20        25        30

Arg Ala Tyr Leu Glu Cys Ala Leu His Thr Asp Met Ala Asp Ile Glu
    35        40        45

Gln Tyr Tyr Met Lys Pro Pro Gly Ser Cys Phe Trp Val Ala Val Leu
50        55        60

Asp Gly Asn Val Val Gly Ile Val Ala Ala Arg Ala His Glu Glu Asp
65       70        75        80

Asn Thr Val Glu Leu Leu Arg Met Ser Val Asp Ser Arg Phe Arg Gly
      85        90        95

Lys Gly Ile Ala Lys Ala Leu Gly Arg Lys Val Leu Glu Phe Ala Val
        100       105       110

Val His Asn Tyr Ser Ala Val Val Leu Gly Thr Thr Ala Val Lys Val
    115        120       125

Ala Ala His Lys Leu Tyr Glu Ser Leu Gly Phe Arg His Met Gly Ala
   130        135        140

<210> SEQ ID NO 9
<211> LENGTH: 1027
<212> TYPE: DNA
<213> ORGANISM: Mus sp.

<400> SEQUENCE: 9

```
attcggcacg acggctaaaa tggaagtgga gcggactcct agtaccgcta gaagctgctg    60
gcggaggaca aggagaacta actctaattt gtcccggctt cggaggtgga aaagccccca   120
ctggtcgggc ctagaagctg agggttcaag gaaggtgtgc aaggcaggta tagctgtctc   180
tcctggatgc caagatttga gacccagaag tctcccatgg ttccttatca catccgacag   240
taccaggaca gcgaccataa aagagtcgtg gatgtgttca ccaagggcat ggaggagtac   300
attccctcta cctttcggca catgcttatg ctgccccgaa ccctcctgct cttacttggg   360
gtgcccttg ccctggtcct ggtgtctggc tcctggatcc tggctgttat ttgcatcttc   420
tttctgctcc tacttctgcg gctccttgcc agacagccct ggaaggaata tgtggccaaa   480
tgtttgcaga cagacatggt tgacatcacc aagtcttacc tgaatgtaca tggcgcctgc   540
ttctgggtgg ctgagtctgg ggggcaggtg gtgggcatag tggctgctca gccagtcaag   600
gatcctccac tagggaggaa gcagctgcag ctctttcgcc tgtctgtgtc ctcacagcat   660
cgaggacagg ggatagcgaa agcgctgacc agaactgtcc tccagtttgc aagggaccag   720
agttacagtg atgttgtcct tgagaccagc gccttgcagc aaggtgctgt gactctctac   780
ctgggcatgg gcttcaagaa ggcaggccag tacttcatga gtatattctg gaggttagca   840
ggtatttgta caattcaatt aaagtactcc ttcccttctg cctaggaggg gtggctgtga   900
ccttatgctc ctgtgcagca agcacacttc tctgcactct gctacaggaa ccagtgaacc   960
ctgtcatgtc agtgtgatta acaataaaag ttgttggtgc acaccaaaaa aaaaaaaaa   1020
aaaaaaa                                                           1027
```

<210> SEQ ID NO 10
<211> LENGTH: 222
<212> TYPE: PRT

<213> ORGANISM: Mus sp.

<400> SEQUENCE: 10

| Met | Val | Pro | Tyr | His | Ile | Arg | Gln | Tyr | Gln | Asp | Ser | Asp | His | Lys | Arg |
|---|---|---|---|---|---|---|---|---|---|---|---|---|---|---|---|
| 1 | | | | 5 | | | | | 10 | | | | | 15 | |

| Val | Val | Asp | Val | Phe | Thr | Lys | Gly | Met | Glu | Glu | Tyr | Ile | Pro | Ser | Thr |
|---|---|---|---|---|---|---|---|---|---|---|---|---|---|---|---|
| | | | 20 | | | | | 25 | | | | | 30 | | |

| Phe | Arg | His | Met | Leu | Met | Leu | Pro | Arg | Thr | Leu | Leu | Leu | Leu | Leu | Gly |
|---|---|---|---|---|---|---|---|---|---|---|---|---|---|---|---|
| | | 35 | | | | | 40 | | | | | 45 | | | |

| Val | Pro | Leu | Ala | Leu | Val | Leu | Val | Ser | Gly | Ser | Trp | Ile | Leu | Ala | Val |
|---|---|---|---|---|---|---|---|---|---|---|---|---|---|---|---|
| | 50 | | | | | 55 | | | | | 60 | | | | |

| Ile | Cys | Ile | Phe | Phe | Leu | Leu | Leu | Leu | Arg | Leu | Leu | Ala | Arg | Gln | |
|---|---|---|---|---|---|---|---|---|---|---|---|---|---|---|---|
| 65 | | | | | 70 | | | | | 75 | | | | | 80 |

| Pro | Trp | Lys | Glu | Tyr | Val | Ala | Lys | Cys | Leu | Gln | Thr | Asp | Met | Val | Asp |
|---|---|---|---|---|---|---|---|---|---|---|---|---|---|---|---|
| | | | | 85 | | | | | 90 | | | | | 95 | |

| Ile | Thr | Lys | Ser | Tyr | Leu | Asn | Val | His | Gly | Ala | Cys | Phe | Trp | Val | Ala |
|---|---|---|---|---|---|---|---|---|---|---|---|---|---|---|---|
| | | | 100 | | | | | 105 | | | | | 110 | | |

| Glu | Ser | Gly | Gly | Gln | Val | Val | Gly | Ile | Val | Ala | Ala | Gln | Pro | Val | Lys |
|---|---|---|---|---|---|---|---|---|---|---|---|---|---|---|---|
| | | 115 | | | | | 120 | | | | | 125 | | | |

| Asp | Pro | Pro | Leu | Gly | Arg | Lys | Gln | Leu | Gln | Leu | Phe | Arg | Leu | Ser | Val |
|---|---|---|---|---|---|---|---|---|---|---|---|---|---|---|---|
| | 130 | | | | | 135 | | | | | 140 | | | | |

| Ser | Ser | Gln | His | Arg | Gly | Gln | Gly | Ile | Ala | Lys | Ala | Leu | Thr | Arg | Thr |
|---|---|---|---|---|---|---|---|---|---|---|---|---|---|---|---|
| 145 | | | | | 150 | | | | | 155 | | | | | 160 |

| Val | Leu | Gln | Phe | Ala | Arg | Asp | Gln | Ser | Tyr | Ser | Asp | Val | Val | Leu | Glu |
|---|---|---|---|---|---|---|---|---|---|---|---|---|---|---|---|
| | | | | 165 | | | | | 170 | | | | | 175 | |

| Thr | Ser | Ala | Leu | Gln | Gln | Gly | Ala | Val | Thr | Leu | Tyr | Leu | Gly | Met | Gly |
|---|---|---|---|---|---|---|---|---|---|---|---|---|---|---|---|
| | | | 180 | | | | | 185 | | | | | 190 | | |

| Phe | Lys | Lys | Ala | Gly | Gln | Tyr | Phe | Met | Ser | Ile | Phe | Trp | Arg | Leu | Ala |
|---|---|---|---|---|---|---|---|---|---|---|---|---|---|---|---|
| | | 195 | | | | | 200 | | | | | 205 | | | |

| Gly | Ile | Cys | Thr | Ile | Gln | Leu | Lys | Tyr | Ser | Phe | Pro | Ser | Ala | | |
|---|---|---|---|---|---|---|---|---|---|---|---|---|---|---|---|
| | 210 | | | | | 215 | | | | | 220 | | | | |

<210> SEQ ID NO 11
<211> LENGTH: 1080
<212> TYPE: DNA
<213> ORGANISM: Mus sp.

<400> SEQUENCE: 11

| | | | | | |
|---|---|---|---|---|---|
| gaggttcacc | aggctctggt | aggttttact | ggatgtcatc | ggaggcaaag | gccatcctgg | 60 |
| acatttggat | ctgtcatatt | agactgaatc | attccagttg | ctggaaagag | gatttgttga | 120 |
| aacttggacc | tgggaacaca | ggagttttca | actctgggcc | ctgaagagga | aacagaagat | 180 |
| ctcagaacag | cacatctttc | cacagtgtag | aacctcagtt | cccaaagggc | tcagggaagt | 240 |
| tatgcaagaa | ggtctggatg | tcccttgtga | tcactgatac | ttgagagcca | gaagtctccc | 300 |
| catggctgct | tatcacatcc | gacagtacca | ggagaaggac | cacaaagggg | tcctggaatt | 360 |
| gttctccagc | ggcatgaagg | agcttattcc | tgctgccatc | cgacagatgc | tgacactgcc | 420 |
| tcattctctc | ttgctcttac | ctggagtgcc | tgtgaccata | gtattgatgt | ctgcctcctg | 480 |
| gctcctggcc | acattataca | gcttcctctt | tctcctttgc | ctgtggctta | ttttctggat | 540 |
| ttcttgcaga | aattatgtgg | ctaaaagttt | gcaggcagat | cttgctgaca | tcaccaagtc | 600 |
| ttacctgaat | gcacatggct | ccttctgggt | ggctgagtct | ggagaccaag | tagttggcat | 660 |
| ggtgggtgct | cagccagtca | aggaccctcc | attagggaag | aagcagatgc | agctctttcg | 720 |
| cctgtctgtg | tcctcacagc | atcgaggaca | gggaatagca | aaggcactgg | tcagaactct | 780 |

```
cctccagttt gctcgggacc agggttacag tgatgttgtc cttgagactg gcagtgtgca    840
acatagtgct caggctctct accaggccat gggcttccag aagacaggcc agtactttgt    900
cagtataagc aagaagttaa tgggtctttc tattcttcaa ttctcttact ctctcccttt    960
tgcttcagga ccagggtata gtgggaaata tttaaaaaaa ggtcccattc catgctagca   1020
ccaggtactc tctggcccca gtggtctcac tgcctccatg gcttgtccta tgtagcaact   1080
```

<210> SEQ ID NO 12
<211> LENGTH: 238
<212> TYPE: PRT
<213> ORGANISM: Mus sp.

<400> SEQUENCE: 12

```
Met Ala Ala Tyr His Ile Arg Gln Tyr Gln Glu Lys Asp His Lys Arg
1               5                   10                  15

Val Leu Glu Leu Phe Ser Ser Gly Met Lys Glu Leu Ile Pro Ala Ala
            20                  25                  30

Ile Arg Gln Met Leu Thr Leu Pro His Ser Leu Leu Leu Leu Pro Gly
        35                  40                  45

Val Pro Val Thr Ile Val Leu Met Ser Ala Ser Trp Leu Leu Ala Thr
    50                  55                  60

Leu Tyr Ser Phe Leu Phe Leu Leu Cys Leu Trp Leu Ile Phe Trp Ile
65                  70                  75                  80

Ser Cys Arg Asn Tyr Val Ala Lys Ser Leu Gln Ala Asp Leu Ala Asp
                85                  90                  95

Ile Thr Lys Ser Tyr Leu Asn Ala His Gly Ser Phe Trp Val Ala Glu
            100                 105                 110

Ser Gly Asp Gln Val Val Gly Met Val Gly Ala Gln Pro Val Lys Asp
        115                 120                 125

Pro Pro Leu Gly Lys Lys Gln Met Gln Leu Phe Arg Leu Ser Val Ser
    130                 135                 140

Ser Gln His Arg Gly Gln Gly Ile Ala Lys Ala Leu Val Arg Thr Leu
145                 150                 155                 160

Leu Gln Phe Ala Arg Asp Gln Gly Tyr Ser Asp Val Val Leu Glu Thr
                165                 170                 175

Gly Ser Val Gln His Ser Ala Gln Ala Leu Tyr Gln Ala Met Gly Phe
            180                 185                 190

Gln Lys Thr Gly Gln Tyr Phe Val Ser Ile Ser Lys Lys Leu Met Gly
        195                 200                 205

Leu Ser Ile Leu Gln Phe Ser Tyr Ser Leu Pro Phe Ala Ser Gly Pro
    210                 215                 220

Gly Tyr Ser Gly Lys Tyr Leu Lys Lys Gly Pro Ile Pro Cys
225                 230                 235
```

<210> SEQ ID NO 13
<211> LENGTH: 938
<212> TYPE: DNA
<213> ORGANISM: Mus sp.

<400> SEQUENCE: 13

```
attcggatcc atggcacagc attaaggctg atttggaccc tgagctctga gcaactagtc     60
taaatgttca gagctgatgg gaatggcttt gttgaaact tgatcttgga atcctgcat     120 ttgcaatgta tatactctag agaaagagat caaaggagct gggcatgaag actggtggcc    180
tcaagggtta cagggaaacc tacagtcaga agcagctgtg tctttggtct ttgagatctt    240
```

-continued

```
agcctccgaa gtctcccatg gctccttatc atatccgaaa ataccaggac agcgaccaca    300
ggagtgtggt ggatttgttc cgcagaggca tggaggagca catccccgct acctttcgcc    360
acatgctgct gctgccccga accctcctgc tcttactcgg ggtccctctt actctattcc    420
tggcctcagg ttcctggctt ctggttcttc tgtccatcct taccctcttt ctttccctgt    480
ggttccttgc aaaatacaca tgggaaaagc atgtgatgaa ctgtttgcac acagacatgg    540
ctgacatcac cagaacctac ctgagttctc actcctcctg cttctgggta gctgagtcta    600
gaggtcagac agtgggcatg gtggctgctc ggccagtgaa ggaccccctc ctgcagaaga    660
agcaactgca gctacttcac ctctctgtgt cattgcagca ccgaagagaa ggcctaggga    720
aagctatggt caggactgtc ctccaatttg cacagatgca gggcttcagt gaagttgtcc    780
tttccaccag catgctgcag tacgcagccc tggctctcta ccagggcatg ggcttccaga    840
agactggcga gaccttctac acctatttgt ccagactaag gaaatctcca atgataaact    900
taaagtatag cctcacttct cgggaagggg acctgtga                            938
```

<210> SEQ ID NO 14
<211> LENGTH: 226
<212> TYPE: PRT
<213> ORGANISM: Mus sp.

<400> SEQUENCE: 14

```
Met Ala Pro Tyr His Ile Arg Lys Tyr Gln Asp Ser Asp His Arg Ser
1               5                   10                  15

Val Val Asp Leu Phe Arg Arg Gly Met Glu Glu His Ile Pro Ala Thr
            20                  25                  30

Phe Arg His Met Leu Leu Leu Pro Arg Thr Leu Leu Leu Leu Leu Gly
        35                  40                  45

Val Pro Leu Thr Leu Phe Leu Ala Ser Gly Ser Trp Leu Leu Val Leu
    50                  55                  60

Leu Ser Ile Leu Thr Leu Phe Leu Ser Leu Trp Phe Leu Ala Lys Tyr
65                  70                  75                  80

Thr Trp Glu Lys His Val Met Asn Cys Leu His Thr Asp Met Ala Asp
                85                  90                  95

Ile Thr Arg Thr Tyr Leu Ser Ser His Ser Ser Cys Phe Trp Val Ala
            100                 105                 110

Glu Ser Arg Gly Gln Thr Val Gly Met Val Ala Ala Arg Pro Val Lys
        115                 120                 125

Asp Pro Leu Leu Gln Lys Lys Gln Leu Gln Leu Leu His Leu Ser Val
    130                 135                 140

Ser Leu Gln His Arg Arg Glu Gly Leu Gly Lys Ala Met Val Arg Thr
145                 150                 155                 160

Val Leu Gln Phe Ala Gln Met Gln Gly Phe Ser Glu Val Val Leu Ser
                165                 170                 175

Thr Ser Met Leu Gln Tyr Ala Ala Leu Ala Leu Tyr Gln Gly Met Gly
            180                 185                 190

Phe Gln Lys Thr Gly Glu Thr Phe Tyr Thr Tyr Leu Ser Arg Leu Arg
        195                 200                 205

Lys Ser Pro Met Ile Asn Leu Lys Tyr Ser Leu Thr Ser Arg Glu Gly
    210                 215                 220

Asp Leu
225
```

<210> SEQ ID NO 15
<211> LENGTH: 903
<212> TYPE: DNA
<213> ORGANISM: Mus sp.

<400> SEQUENCE: 15

```
ttcggatcca tgggacactc ggctgtagta gcagctaaga ggacagagag acaagggctg      60
cgaggcacaa atataaacag atctggtgtc tctcatggat gctgagattt gagacgaagt     120
ttccccatgg cttcttttcg catccgccag ttccaggaga gggactacaa acaggtcgtg     180
gatgtgttct ccagggcat ggaggagcac atacccactg ccttccgcca cttgctgaca     240
ctgccccgaa ccctcctgct cttagctgtg gtgcccttg ccatagtcct ggtgtctggc     300
tcctggttcc tggctgttgt atgcattttc tttctgttcc tattcttgtg gttcctcgcc     360
agcaagccct ggaagaatta tgtgtccaaa tgtttacaca cagacatggc tgacatcacc     420
aagtcctacc tgagtgtccg tggctcaggt ttctgggtgg ctgagtctgg ggggcaggtg     480
gtgggtacag tggctgctcg gccagtcaag gatcctccgt tagggaggaa gcagctgcag     540
ctctttcgcc tgtctgtgtc ctcacagcat cgaggacagg ggatagcgaa agcgctgacc     600
agaactgtcc tccagtttgc aagggaccag ggttacagtg atgttgtcct tgtgactggc     660
cttttgcagc aaggtgctgt gactctctac tacagcatgg gcttccagaa gacaggtgaa     720
tccttcgtgg acatactcac atggcttgtg gatgtttctc taattcattt catataccca     780
ctcccttctg ctcaaaaata tgagttgtga tctctctcag tgtgtctgtc agcctctggt     840
ttactatgct gtgggaataa ataacccaga gattgtggtg gacaaatcaa aaaaaaagg     900
aaa                                                                   903
```

<210> SEQ ID NO 16
<211> LENGTH: 227
<212> TYPE: PRT
<213> ORGANISM: Mus sp.

<400> SEQUENCE: 16

```
Met Ala Ser Phe Arg Ile Arg Gln Phe Gln Glu Arg Asp Tyr Lys Gln
1               5                   10                  15

Val Val Asp Val Phe Ser Arg Gly Met Glu Glu His Ile Pro Thr Ala
            20                  25                  30

Phe Arg His Leu Leu Thr Leu Pro Arg Thr Leu Leu Leu Ala Val
        35                  40                  45

Val Pro Leu Ala Ile Val Leu Val Ser Gly Ser Trp Phe Leu Ala Val
    50                  55                  60

Val Cys Ile Phe Leu Phe Leu Phe Leu Trp Phe Leu Ala Ser Lys
65                  70                  75                  80

Pro Trp Lys Asn Tyr Val Ser Lys Cys Leu His Thr Asp Met Ala Asp
                85                  90                  95

Ile Thr Lys Ser Tyr Leu Ser Val Arg Gly Ser Gly Phe Trp Val Ala
            100                 105                 110

Glu Ser Gly Gly Gln Val Val Gly Thr Val Ala Ala Arg Pro Val Lys
        115                 120                 125

Asp Pro Pro Leu Gly Arg Lys Gln Leu Gln Leu Phe Arg Leu Ser Val
    130                 135                 140

Ser Ser Gln His Arg Gly Gln Gly Ile Ala Lys Ala Leu Thr Arg Thr
145                 150                 155                 160

Val Leu Gln Phe Ala Arg Asp Gln Gly Tyr Ser Asp Val Val Leu Val
                165                 170                 175
```

Thr Gly Leu Leu Gln Gln Gly Ala Val Thr Leu Tyr Tyr Ser Met Gly
            180                 185                 190

Phe Gln Lys Thr Gly Glu Ser Phe Val Asp Ile Leu Thr Trp Leu Val
        195                 200                 205

Asp Val Ser Leu Ile His Phe Ile Tyr Pro Leu Pro Ser Ala Gln Lys
    210                 215                 220

Tyr Glu Leu
225

<210> SEQ ID NO 17
<211> LENGTH: 358
<212> TYPE: DNA
<213> ORGANISM: Mus sp.

<400> SEQUENCE: 17
caaagtgcta taaccctcta tgaggctatg ggattccaaa ggacaggaaa atactcagag      60
atcagcatta tcaaatggtt aattacattt ctataattc atttcacata ttctttccct     120
tctactcaga acatgaact ataatcttat ttcttaccat atagatcagg ttccaattac     180
tgtactgtaa taaataataa agcatatttt ttcatgctca ccggattact acttgacaat    240
gttagggtga caaagttgac ctctacagtg cacagccctt ctccatgaga catttgtttc    300
atctttgaga tcctttccgg gggctacttt gcatctctac tcttattaaa ctgagcat     358

<210> SEQ ID NO 18
<211> LENGTH: 47
<212> TYPE: PRT
<213> ORGANISM: Mus sp.

<400> SEQUENCE: 18

Gln Ser Ala Ile Thr Leu Tyr Glu Ala Met Gly Phe Gln Arg Thr Gly
1               5                   10                  15

Lys Tyr Ser Glu Ile Ser Ile Lys Trp Leu Ile Thr Phe Ser Ile
            20                  25                  30

Ile His Phe Thr Tyr Ser Phe Pro Ser Thr Gln Lys His Glu Leu
        35                  40                  45

<210> SEQ ID NO 19
<211> LENGTH: 916
<212> TYPE: DNA
<213> ORGANISM: Rattus sp.

<400> SEQUENCE: 19
ttcggcacga ggccactgaa tgccactaga agctgatgcc attccagaca ctctaggttg      60
tgtagtagcg ggactcaggg aaggagtgtg ggcaagtgaa tgctgagatt tgagacccag    120
aagtttctcc catggtttct tatcacatct gcgagtacca agacagcgac tataaaagtg    180
ttgtggatgt gtttaccaag ggtgcagaag agtacatccc ctccaccttc cgccacttgc    240
tgctgctgcc ccgaaccctc ctactcttac ttggggtgtc ccttgccctg gtcctggtgt    300
ctggctcctg gctgctggct gttgtatgca tcttttttct gctcccattt tgtggttcc    360 ttgctggaca gccctggaag aattatgtgt ccaaatgttt acacacagat atggctgaca    420
tcaccaagtc ttatctgagt gatcgtggct caggtttctg ggtggctgag tctggggagc    480
aggtagtggg cacagtgggt gctctgccag tcaaggagcc tccatcaggg aggaagcagt    540
tgcagctctt ccacctggct gtgtcctcac agcatcgagg acaggggata gcgaaagcac    600
tggtcagaac tgtgctccag tttgcacggg accagggcta cactgatgtt gtccttgaga    660

```
ctagcaccat gcagataggt gctgtgaccc tctacctggg catgggtttc cagaagacag    720
gccaatactt cccgagtatg ctctggaggt tagtgggtat tcgttttgtt caactaaatt    780
actccttccc ttctgcctag gaagggaggc tgtgaccttg agttcctgtg gagcaagcac    840
acttccctgc actctgctac aggaaccagt gaaccctgtc atgtcagtgt gattaacaac    900
aaaagcttgt tgctgc                                                    916
```

<210> SEQ ID NO 20
<211> LENGTH: 222
<212> TYPE: PRT
<213> ORGANISM: Rattus sp.

<400> SEQUENCE: 20

```
Met Val Ser Tyr His Ile Cys Glu Tyr Gln Asp Ser Asp Tyr Lys Ser
 1               5                  10                  15

Val Val Asp Val Phe Thr Lys Gly Ala Glu Tyr Ile Pro Ser Thr
            20                  25                  30

Phe Arg His Leu Leu Leu Leu Pro Arg Thr Leu Leu Leu Leu Gly
        35                  40                  45

Val Ser Leu Ala Leu Val Leu Val Ser Gly Ser Trp Leu Leu Ala Val
50                  55                  60

Val Cys Ile Phe Phe Leu Leu Pro Phe Leu Trp Phe Leu Ala Gly Gln
65                  70                  75                  80

Pro Trp Lys Asn Tyr Val Ser Lys Cys Leu His Thr Asp Met Ala Asp
                85                  90                  95

Ile Thr Lys Ser Tyr Leu Ser Asp Arg Gly Ser Gly Phe Trp Val Ala
            100                 105                 110

Glu Ser Gly Glu Gln Val Val Gly Thr Val Gly Ala Leu Pro Val Lys
        115                 120                 125

Glu Pro Pro Ser Gly Arg Lys Gln Leu Gln Leu Phe His Leu Ala Val
    130                 135                 140

Ser Ser Gln His Arg Gly Gln Gly Ile Ala Lys Ala Leu Val Arg Thr
145                 150                 155                 160

Val Leu Gln Phe Ala Arg Asp Gln Gly Tyr Thr Asp Val Val Leu Glu
                165                 170                 175

Thr Ser Thr Met Gln Ile Gly Ala Val Thr Leu Tyr Leu Gly Met Gly
            180                 185                 190

Phe Gln Lys Thr Gly Gln Tyr Phe Pro Ser Met Leu Trp Arg Leu Val
        195                 200                 205

Gly Ile Arg Phe Val Gln Leu Asn Tyr Ser Phe Pro Ser Ala
    210                 215                 220
```

<210> SEQ ID NO 21
<211> LENGTH: 900
<212> TYPE: DNA
<213> ORGANISM: Rattus sp.

<400> SEQUENCE: 21

```
tcccggcttc ggaagcagaa agcaccctac aggttgggcc tagtagttga gggttcaggg     60
ataggtatag ctgtctctcc tggatgccaa gatttgagac ccagaagtct cccatggctc    120
cttatcacat ccgccagtac aagacagcg accacaaaag tgtcgtggat gtgttcacca    180
agggcatgga agaacacatc ccctccacct tccgccacat gcttatgctg ccccgaaccc    240
tcctactctt acttggggtg ccccttgccc tggtcctggt gtctggctcc tggctgctgg    300
```

-continued

```
ctgttgtatg catcttcttt ctgctcctac tcctgcggtt ccttgctgga cagccctgga      360
aggagtatgt ggctacatgt ttgcggacag acatggctga catcaccaag tcttacctga      420
atgcacatgg ctccttctgg gtggctgagt ctggaaacca ggtggtgggc atagtggctg      480
ctctgccagt caaggatcct ccatcaggga ggaagcagct gcagctcttt cgcctgtctg      540
tgtcctcaca gcatcgagga cagggggtag cgaaagcact ggtcagaact gtcctccagt      600
ttgcacggga ccagggctac actgatgttg tccttgagac cagtaccttg caacaaggtg      660
ctatgaccct ctacctgggc atgggcttcc agaagacagg ccaacgcttc ctgactatgt      720
tctggaggtt agtgggtatt cggacaattc aattaaagta tccctccct tctgcctagg       780 aaagggggct gtgaccttga gttcctgtgg agcaagcatg cttctctaaa ctctgctaca      840
ggaaccagtg aaccctgtca tgtcagtgtg attaacaata aaagcttgtt gctgcacacc      900
```

<210> SEQ ID NO 22
<211> LENGTH: 221
<212> TYPE: PRT
<213> ORGANISM: Rattus sp.

<400> SEQUENCE: 22

```
Met Ala Pro Tyr His Ile Arg Gln Tyr Gln Asp Ser Asp His Lys Ser
1               5                   10                  15

Val Val Asp Val Phe Thr Lys Gly Met Glu Glu His Ile Pro Ser Thr
                20                  25                  30

Phe Arg His Met Leu Met Leu Pro Arg Thr Leu Leu Leu Leu Gly
            35                  40                  45

Val Pro Leu Ala Leu Val Leu Val Ser Gly Ser Trp Leu Leu Ala Val
        50                  55                  60

Val Cys Ile Phe Phe Leu Leu Leu Leu Arg Phe Leu Ala Gly Gln
65                  70                  75                  80

Pro Trp Lys Glu Tyr Val Ala Thr Cys Leu Arg Thr Asp Met Ala Asp
                85                  90                  95

Ile Thr Lys Ser Tyr Leu Asn Ala His Gly Ser Phe Trp Val Ala Glu
            100                 105                 110

Ser Gly Asn Gln Val Val Gly Ile Val Ala Ala Leu Pro Val Lys Asp
        115                 120                 125

Pro Pro Ser Gly Arg Lys Gln Leu Gln Leu Phe Arg Leu Ser Val Ser
    130                 135                 140

Ser Gln His Arg Gly Gln Gly Ile Ala Lys Ala Leu Val Arg Thr Val
145                 150                 155                 160

Leu Gln Phe Ala Arg Asp Gln Gly Tyr Thr Asp Val Val Leu Glu Thr
                165                 170                 175

Ser Thr Leu Gln Gln Gly Ala Met Thr Leu Tyr Leu Gly Met Gly Phe
            180                 185                 190

Gln Lys Thr Gly Gln Arg Phe Leu Thr Met Phe Trp Arg Leu Val Gly
        195                 200                 205

Ile Arg Thr Ile Gln Leu Lys Tyr Pro Phe Pro Ser Ala
    210                 215                 220
```

<210> SEQ ID NO 23
<211> LENGTH: 947
<212> TYPE: DNA
<213> ORGANISM: Rattus sp.

<400> SEQUENCE: 23

```
tgtcaggcca agaattcggc acgaggagga cagcgaccac aggagtgtag tgaatttgtt       60
```

-continued

```
ctgcagaggc acggaggagc acatctccgc cagcttccgc tacatgctgc tgctgcccgg    120
aaccctcctg atcttactcg gggtccctct tactctattc ttggcctcag gctcctggct    180
tctggttctt ctgtccaccc taaccctcct tgtttccctg tggctccttg caaaatcccc    240
ttgggagaag tatacggcaa tgtgtttgca ctcagacatg gctgatatcc ccagaaccta    300
cttgagttct cattactcct gcttctgggt ggctgagtct agaggtcaga tggtgggcat    360
aatcgctgtt ttaccagtga aggatcccct cctgcagagg aagcaactgc agctacgtca    420
cctctctgtg tccctggagc accggagaga ggggattgga agagctatgg tcaggactgc    480
cctccagttt gcagagatgc agggcttcag tgaagttgtc ctggtcacca gcatgttgca    540
gtatgctgcc ctagctctgt accagagcat gggcttccag aagactggtg agttcttcta    600
tacctttgtc tctcgactaa ggaattctcc aatgatatgc ttaaaatatt gcctcacttc    660
tgctctgaat gacctgaaaa cctgaaagac ctgctctgag agacctgtga gctctctcct    720
gtggccatca gtcaggatct aattgcttct gtaatagtaa caagcaaacc cagctatttc    780
agcaaaccac tgaccctcac tctcaagcac atcggaataa atgtttgtgg atggggttgg    840
ggcaatggct actctttgtt atccatgctt ttctgaggta tcctttagct aatactacaa    900
tcatatataa aaagtaacgc agataataaa atttaactta gcttgtg                  947
```

<210> SEQ ID NO 24  
<211> LENGTH: 228  
<212> TYPE: PRT  
<213> ORGANISM: Rattus sp.

<400> SEQUENCE: 24

```
Met Val Arg Pro Arg Ile Arg His Glu Glu Asp Ser Asp His Arg Ser
1               5                   10                  15

Val Val Asn Leu Phe Cys Arg Gly Thr Glu Glu His Ile Ser Ala Ser
            20                  25                  30

Phe Arg Tyr Met Leu Leu Leu Pro Gly Thr Leu Leu Ile Leu Leu Gly
        35                  40                  45

Val Pro Leu Thr Leu Phe Leu Ala Ser Gly Ser Trp Leu Leu Val Leu
    50                  55                  60

Leu Ser Thr Leu Thr Leu Leu Val Ser Leu Trp Leu Leu Ala Lys Tyr
65                  70                  75                  80

Pro Trp Glu Lys Tyr Thr Ala Met Cys Leu His Ser Asp Met Ala Asp
            85                  90                  95

Ile Pro Arg Thr Tyr Leu Ser Ser His Tyr Ser Cys Phe Trp Val Ala
        100                 105                 110

Glu Ser Arg Gly Gln Met Val Gly Ile Ile Ala Val Leu Pro Val Lys
    115                 120                 125

Asp Pro Leu Leu Gln Arg Lys Gln Leu Gln Leu Arg His Leu Ser Val
    130                 135                 140

Ser Leu Glu His Arg Arg Glu Gly Ile Gly Arg Ala Met Val Arg Thr
145                 150                 155                 160

Ala Leu Gln Phe Ala Glu Met Gln Gly Phe Ser Glu Val Val Leu Val
            165                 170                 175

Thr Ser Met Leu Gln Tyr Ala Ala Leu Ala Leu Tyr Gln Ser Met Gly
        180                 185                 190

Phe Gln Lys Thr Gly Glu Phe Phe Tyr Thr Phe Val Ser Arg Leu Arg
    195                 200                 205

Asn Ser Pro Met Ile Cys Leu Lys Tyr Cys Leu Thr Ser Ala Leu Asn
```

Asp Leu Lys Thr
225

<210> SEQ ID NO 25
<211> LENGTH: 779
<212> TYPE: DNA
<213> ORGANISM: Rattus sp.

<400> SEQUENCE: 25

| | | | | | |
|---|---|---|---|---|---|
| agacgaaggt | ttcccatggc | ttcttttcac | atccgccagt | tccaggagag | ggactatgaa | 60 |
| caggtcgtgg | atatgttctc | caggggaatg | aaggaacaca | tccccactgc | cttccgccac | 120 |
| ttgctgctgc | tgccccgaac | cctcctactc | ttacttgggg | tgccccttgc | cctggtcctg | 180 |
| gtgtctggct | cctggctgct | ggctgttgta | tgcatcttct | ttctgctccc | attttttgtgg | 240 |
| ttccttgctg | gacagccctg | gaagaattat | gtgtccaaat | gcttacacac | agacatggct | 300 |
| gacatcacca | agtcttatct | gagtgatcgt | ggctcaggtt | tctgggtggc | tgagtctggg | 360 |
| ggccagatag | tgggcacagt | gggtgctctg | ccagtcaagg | atcctccatc | agggaggaag | 420 |
| cagttgcagc | tcttccgcct | gtctgtgtcc | tcacagcatc | gaggacaggg | gatagcgaaa | 480 |
| gcactggtca | gaactgtgct | ccagtttgca | cgggaccagg | gctacacgga | tgttgtcctt | 540 |
| gtgactggcc | ttttgcagca | aggtgctgtg | accctctact | acagcatggg | cttccagaag | 600 |
| acaggcgaat | ccttcatgga | catactcaca | tggcttgtgg | atgtttctct | aattcatttc | 660 |
| atatacccgc | tcccttcctc | ctgagaacct | gagtttcgat | ccctctgtgt | gtctgtcagc | 720 |
| ctctggttca | ctgtgctgtg | ggaacaaata | atcctgatat | tgtagtggac | aaatcaccc | 779 |

<210> SEQ ID NO 26
<211> LENGTH: 222
<212> TYPE: PRT
<213> ORGANISM: Rattus sp.

<400> SEQUENCE: 26

Met Ala Ser Phe His Ile Arg Gln Phe Gln Glu Arg Asp Tyr Glu Gln
1               5                   10                  15

Val Val Asp Met Phe Ser Arg Gly Met Lys Glu His Ile Pro Thr Ala
            20                  25                  30

Phe Arg His Leu Leu Leu Leu Pro Arg Thr Leu Leu Leu Leu Leu Gly
        35                  40                  45

Val Pro Leu Ala Leu Val Leu Val Ser Gly Ser Trp Leu Leu Ala Val
    50                  55                  60

Val Cys Ile Phe Phe Leu Leu Pro Phe Leu Trp Phe Leu Ala Gly Gln
65                  70                  75                  80

Pro Trp Lys Asn Tyr Val Ser Lys Cys Leu His Thr Asp Met Ala Asp
                85                  90                  95

Ile Thr Lys Ser Tyr Leu Ser Asp Arg Gly Ser Gly Phe Trp Val Ala
            100                 105                 110

Glu Ser Gly Gly Gln Ile Val Gly Thr Val Gly Ala Leu Pro Val Lys
        115                 120                 125

Asp Pro Pro Ser Gly Arg Lys Gln Leu Gln Leu Phe Arg Leu Ser Val
    130                 135                 140

Ser Ser Gln His Arg Gly Gln Gly Ile Ala Lys Ala Leu Val Arg Thr
145                 150                 155                 160

Val Leu Gln Phe Ala Arg Asp Gln Gly Tyr Thr Asp Val Val Leu Val
                165                 170                 175

```
-continued

Thr Gly Leu Leu Gln Gln Gly Ala Val Thr Leu Tyr Tyr Ser Met Gly
            180                 185                 190

Phe Gln Lys Thr Gly Glu Ser Phe Met Asp Ile Leu Thr Trp Leu Val
        195                 200                 205

Asp Val Ser Leu Ile His Phe Ile Tyr Pro Leu Pro Ser Ser
    210                 215                 220
```